(12) United States Patent
Gee et al.

(10) Patent No.: US 11,493,446 B2
(45) Date of Patent: Nov. 8, 2022

(54) METHODS AND COMPOSITIONS FOR ASSESSING CELL VIABILITY

(71) Applicant: Life Technologies Corporation, Carlsbad, CA (US)

(72) Inventors: Kyle Gee, Springfield, OR (US); Kathleen Kihn, Lorane, OR (US); Yi-Zhen Hu, Eugene, OR (US); Yexin Wu, Eugene, OR (US); Kathleen Free, Cheshire, OR (US)

( * ) Notice: Subject to any disclaimer, the term of this patent is extended or adjusted under 35 U.S.C. 154(b) by 1014 days.

(21) Appl. No.: 16/205,702

(22) Filed: Nov. 30, 2018

(65) Prior Publication Data

US 2019/0195801 A1    Jun. 27, 2019

Related U.S. Application Data

(60) Provisional application No. 62/609,358, filed on Dec. 22, 2017.

(51) Int. Cl.
| | |
|---|---|
| *G01N 21/64* | (2006.01) |
| *C07D 311/82* | (2006.01) |
| *C07D 209/10* | (2006.01) |
| *C07F 15/00* | (2006.01) |
| *C07F 9/24* | (2006.01) |

(52) U.S. Cl.
CPC ....... *G01N 21/6486* (2013.01); *C07D 209/10* (2013.01); *C07D 311/82* (2013.01); *C07F 9/2466* (2013.01); *C07F 15/0093* (2013.01); *G01N 21/6428* (2013.01)

(58) Field of Classification Search
CPC .................................................. G01N 21/6486
See application file for complete search history.

(56) References Cited

PUBLICATIONS

Fienberg H.G., et al., "A Platinum-Based Covalent Viability Reagent for Single-Cell Mass Cytometry," Cytometry Part A, 2012, vol. 81 A, pp. 467-475.

*Primary Examiner* — Golam M Shameem

(57) ABSTRACT

Provided herein are compounds, compositions, kits, uses, and methods for assessing the viability of cells and/or quantifying the amount of live and dead cells in a mixture using differential stains. In some embodiments, the compounds are used in culture media or can function independently of fixation and/or permeabilization. In some embodiments, the compounds comprise a platinum atom. In some embodiments, the compounds comprise a nitrogen mustard moiety.

17 Claims, 13 Drawing Sheets

METHODS AND COMPOSITIONS FOR ASSESSING CELL VIABILITY

I. CROSS-REFERENCE

This application claims the benefit under 35 U.S.C. § 119(e) of U.S. Provisional Application No. 62/609,358, filed Dec. 22, 2017. The entire contents of the aforementioned applications are incorporated by reference herein.

II. FIELD OF THE INVENTION

The present disclosure relates to methods and compositions for assessing cell viability, including differential stains for non-viable cells.

III. INTRODUCTION AND SUMMARY

Dyes for differentially staining live and dead cells are widely used in cell biological and flow cytometric procedures, e.g., to evaluate cytotoxicity in various circumstances. Such dyes can exploit the differential permeability of nonviable cells, which have generally lost membrane integrity. Common dyes for this purpose are generally introduced to cells after extracellular protein (such as occurs in culture media) is removed, to avoid undesired side reactions with those compounds, and may require up to 30 minutes of incubation. It would be desirable to simplify workflow, increase throughput, and/or reduce costs by providing reagents that can function in the presence of extracellular protein or other amine-containing compounds and that can differentially stain cells in shorter times.

The present disclosure provides compositions and methods for detection, differential staining, and quantification of dead (non-viable) cells in which a fluorescent moiety (D) is linked through a linker L (which can be a bond or a longer linker) to a reactive moiety (R). In some embodiments, R comprises a nitrogen mustard as discussed in more detail below. In some embodiments, R comprises a platinum atom as discussed in more detail below. The working examples below show that such compounds can differentially stain live and dead cells in the presence of culture media, i.e., regardless of the presence of extracellular amine-containing compounds, and can provide differential staining for quantification of live and dead cells in substantially less than 30 minutes. The embodiments provided herein include the following, without limitation.

In certain embodiments of the present disclosure, a compound of Formula I is provided, wherein Formula I has the structure:

D-L-R     (Formula I)

wherein:
D is a fluorescent moiety;
L is a linker; and
R is Formula IA or Formula IB:

—B—N($R^1$)($R^2$)     (Formula IA), wherein
B is a bond, an aliphatic group or an aromatic group; and
$R^1$ and $R^2$ are each independently ethyl substituted with a Z at the 2 position, or substituted ethyl further substituted with a Z at the 2 position, and each Z is independently OH, Cl, Br, I or

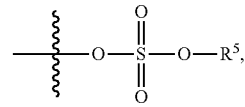

where $R^5$ is alkyl, substituted alkyl, aryl or substituted aryl; or

-A-Pt(X)($R^3$)($R^4$)     (Formula IB), wherein
A is a heterocycloalkyl or substituted heterocycloalkyl in which a nitrogen is bonded to the platinum (Pt) of Formula IB;
the substituents of the platinum of Formula IB are in a square planar configuration with $R^3$ and $R^4$ in cis;
X is Cl, Br, or I;
$R^3$ and $R^4$ are each independently —$NH_2R^6$, wherein $R^6$ is H, $C_{1-6}$ alkyl, or substituted $C_{1-6}$ alkyl; or $R^3$ and $R^4$, together with the platinum of Formula IB, form a ring in which the two atoms bonded to the platinum are nitrogen and the ring comprises at least two carbons between the nitrogens.

In certain embodiments of the compounds provided herein, R is Formula IA. In certain preferred embodiments, B is aryl, substituted aryl, heteroaryl, or substituted heteroaryl. In certain embodiments, R is

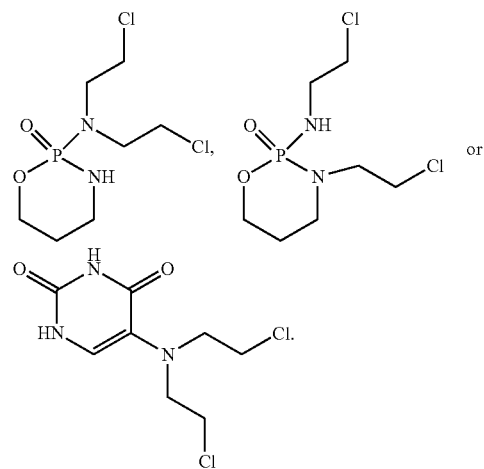

In certain embodiments, B is a six-membered aryl, substituted aryl, heteroaryl, or substituted heteroaryl. In certain embodiments, —N($R^1$)($R^2$) is para to L. In certain preferred embodiments, B is phenyl, substituted phenyl, pyridinyl, or substituted pyridinyl. In some embodiments, $R^1$ and $R^2$ are each independently ethyl substituted with one Z in the 2 position. In certain preferred embodiments, Z is OH or Cl. In certain more preferred embodiments, —N($R^1$)($R^2$) is

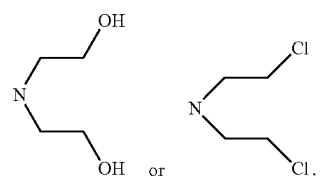 [SMILES: OCCNCCO ; ClCCNCCCl]

In some embodiments, R is

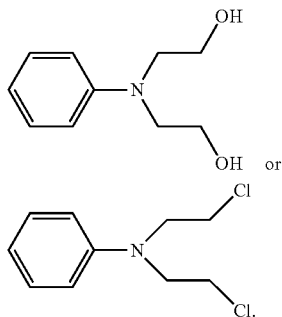

In certain embodiments of the compounds provided herein, R is Formula IB. In certain embodiments, A contains from one to three nitrogens. In certain preferred embodiments, A comprises at least two nitrogens. In certain embodiments, one nitrogen in A, different from the nitrogen bonded to the platinum, is bonded to L. In some embodiments, A is a five-, six-, or seven-membered ring in which a nitrogen is bonded to the platinum of Formula IB. In certain preferred embodiments, A is a six-membered ring in which a nitrogen is bonded to the platinum of Formula IB. In some embodiments, A does not contain more than two nitrogens. In certain embodiments, A is

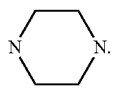

In some embodiments, X is Cl or Br. In some embodiments, $R^3$ and $R^4$, together with the platinum of Formula IB, form a ring in which the two atoms bonded to the platinum are nitrogen and the ring comprises at least one carbon between the nitrogens. In certain embodiments, the ring formed by $R^3$, $R^4$, and the platinum of Formula IB is a four-, five-, six-, or seven-membered ring. In certain embodiments, the ring formed by $R^3$, $R^4$, and the platinum of Formula IB comprises at least two carbons between the nitrogens. In certain embodiments, the ring formed by $R^3$, $R^4$, and the platinum of Formula IB does not comprise more than three carbons between the nitrogens. In some embodiments, the platinum of Formula IB does not comprise more than two carbons between the nitrogens. In some embodiments, the ring formed by $R^3$, $R^4$, and the platinum of Formula IB comprises $L^2$ between the nitrogens bound to the platinum, and $L^2$ is a $C_{1-3}$ alkylene or substituted $C_{1-3}$ alkylene. In certain preferred embodiments, $L^2$ is a methylene, ethylene, or propylene. In certain embodiments, $L^2$ is an ethylene or substituted ethylene. In certain preferred embodiments, $L^2$ is an ethylene. In some embodiments, the ring formed by $R^3$, $R^4$, and the platinum of Formula IB is a five-membered ring. In certain preferred embodiments, the ring formed by $R^3$, $R^4$, and the platinum of Formula IB is

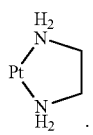

In certain more preferred embodiments, R is

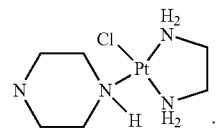

In certain embodiments of the compounds provided herein, L comprises a 1, 2, 3, 4, 5, 6, 7, 8, 9, 10, 11, 12, 13, 14, or 15 atom chain. In certain embodiments, L comprises a 6, 7, 8, 9, 10, 11, 12, or 13 atom chain. In certain embodiments, L comprises an amide. In certain embodiments, the amide is linked to R by a methylene, ethylene, propylene, butylene, or substituted $C_{1-4}$ alkylene. In certain embodiments, the methylene, ethylene, propylene, butylene, or substituted $C_{1-4}$ alkylene links the amide to R through the amide carbonyl. In some embodiments, the amide is linked to R by a propylene. In certain embodiments, L comprises a nitrogen that is bonded to D. In certain embodiments, L comprises an amide that is linked to the nitrogen bonded to D by a propylene, butylene, pentylene, hexylene, or substituted $C_{3-6}$ alkylene. In certain embodiments, L comprises an amide that is linked to the nitrogen bonded to D by a pentylene or substituted pentylene. In some embodiments, the propylene, butylene, pentylene, hexylene, or substituted $C_{3-6}$ alkylene links the amide to D through the amide nitrogen. In certain preferred embodiments, L is

in which (D) and (R) indicate the points of attachment to D and R, respectively. In certain preferred embodiments, L is

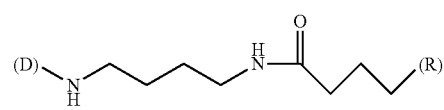

in which (D) and (R) indicate the points of attachment to D and R, respectively. In certain embodiments, L is a bond.

In certain embodiments of the compounds provided herein, the compound has a near infrared, red, orange, yellow, green, cyan, blue, or violet emission maximum.

In certain embodiments of the compounds provided herein, D is Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, or Alexa Fluor® 790.

In certain embodiments of the compounds provided herein, D is a xanthene dye, a cyanine dye, a phenanthridinium dye, a bisbenzimide dye, a bisbenzimidazole dye, an acridine dye, a chromomycinone dye, OliGreen™, PicoGreen™, SYBR™ Green, SYBR™ Green II, SYBR™ Gold, SYBR™ Safe, CyQUANT™ GR, DAPI, ethidium bromide, dihydroethidium, propidium iodide, hexidium iodide, QuantiFluor® ssDNA dye, QuantiFluor® dsDNA dye, a benzothiazolium dye, acridine orange, proflavine HCl, thiazole orange, oxazole yellow, chromomycin A3, 7-aminoactinomycin D, hydroxystilbamidine, Hoechst 33258, Hoechst 33342, thiazole orange tetramethylpropane diamine, thiazole orange tetramethyl diamine, ethidium propane diamine, or ethidium diethylene triamine.

In certain embodiments of the compounds provided herein, the compound comprises at least one, two, or three water-solubilizing groups.

In certain preferred embodiments of the compounds provided herein, the compound is a free acid or salt of any one of:

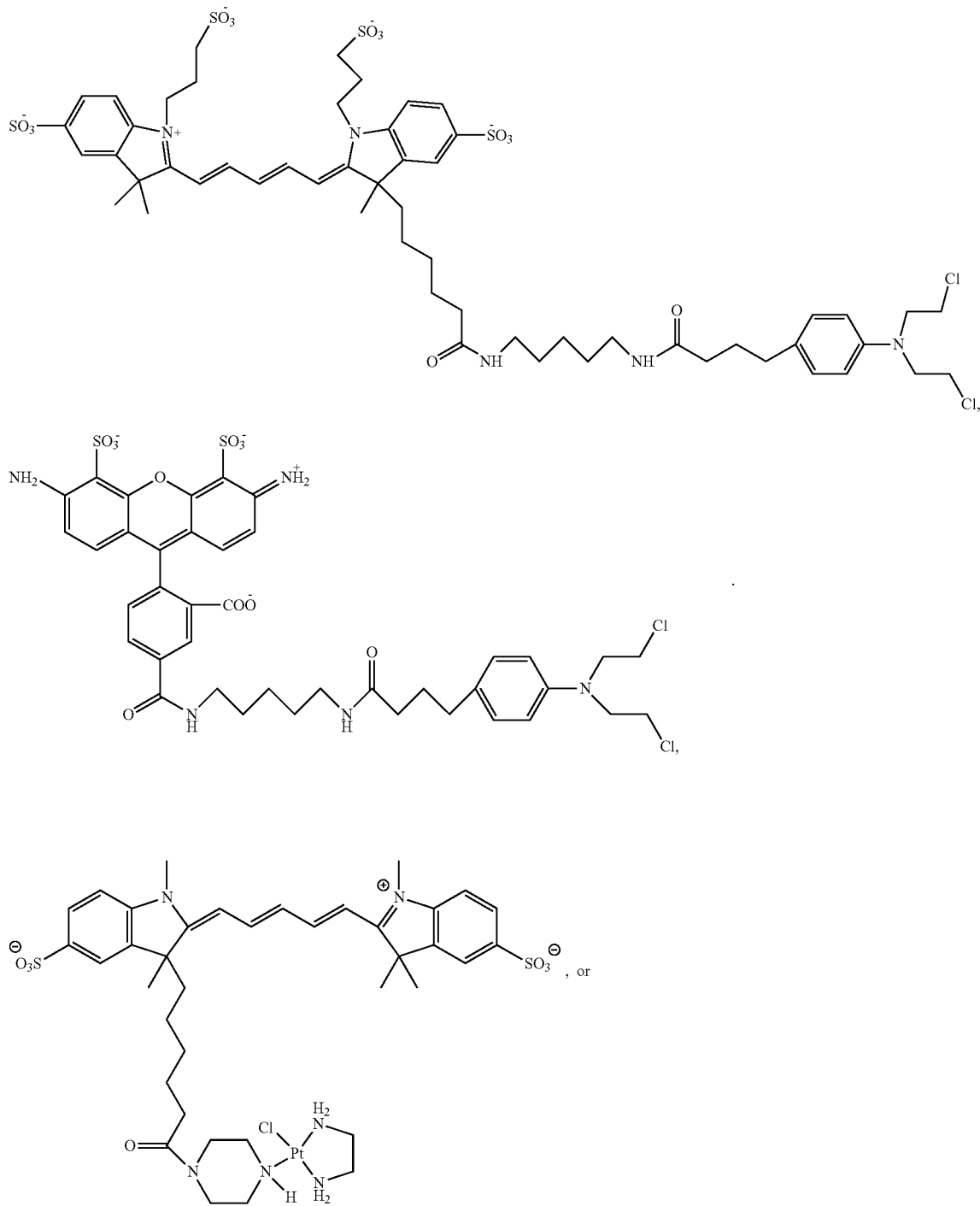

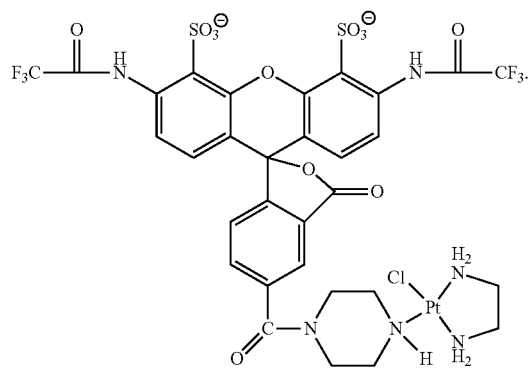
In certain preferred embodiments, the compounds provided herein are
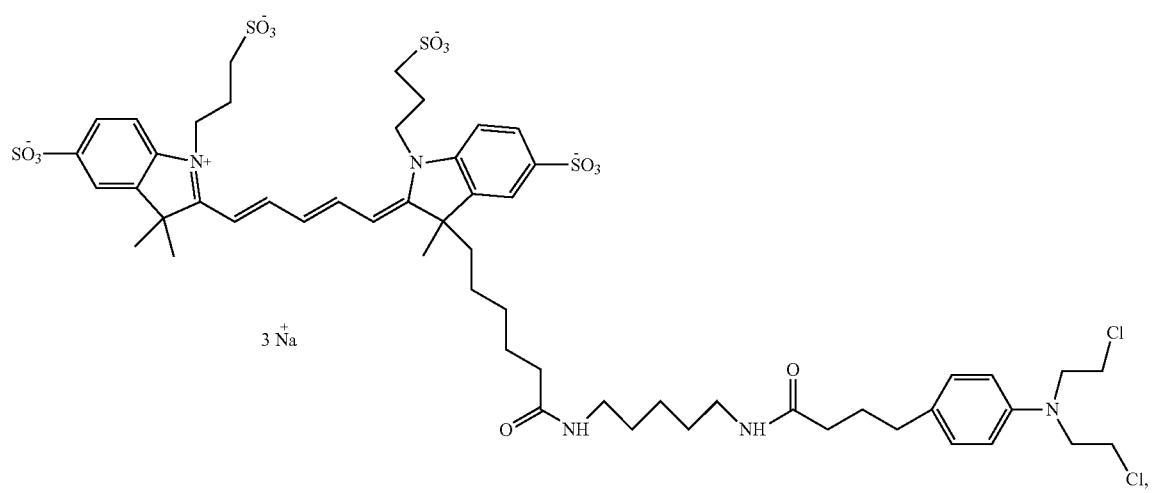
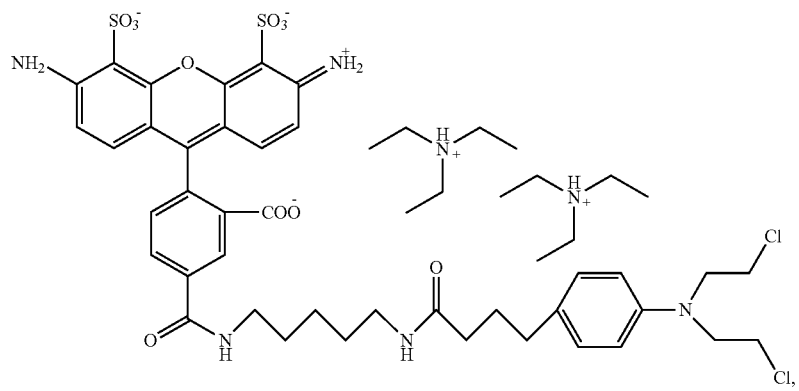

-continued

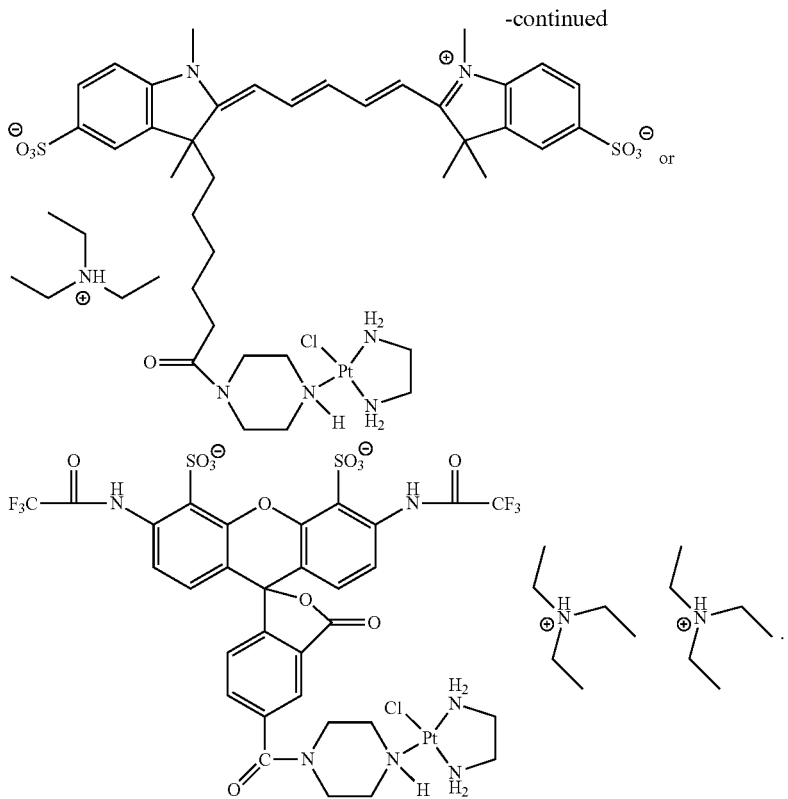

In certain embodiments of the present disclosure, a composition is provided, the composition comprising any of the compounds provided herein and at least one solvent. In certain embodiments, the solvent comprises water or DMSO, or a combination thereof. In certain embodiments, the composition further comprises a culture medium. In certain embodiments, the composition further comprises at least one cell. In certain embodiments, the composition provided herein further comprises at least one dead cell. In certain embodiments, the composition further comprises a mixture of live and dead cells. In certain embodiments, the composition further comprises fixed cells that were a mixture of live and dead cells before fixation. In certain embodiments, the composition further comprises permeabilized cells that were a mixture of live and dead cells before fixation. In certain embodiments, the composition further comprises fixed and permeabilized cells that were a mixture of live and dead cells before fixation.

The present disclosure further provides kits comprising any one of the compounds provided herein or any one of the compositions provided herein.

The present disclosure also provides methods for staining cells or assessing cell viability, comprising the steps of:
 a) incubating a cell or mixture of cells with any one of the compounds provided herein;
 b) providing a stimulus to the cell or mixture of cells to elicit a fluorescent signal; and
 c) measuring the fluorescent signal.

In certain embodiments of the methods provided herein, the method further comprises incubating a mixture of live and dead cells with any one of the compounds provided herein. In certain embodiments, the method further comprises determining the number or proportion of live and/or dead cells in the mixture. In certain embodiments, the incubating step is performed in cell culture media.

The present disclosure also provides methods for assessing cell viability, comprising:
 a) providing a stimulus to any of the compounds or compositions provided herein to elicit a fluorescent signal; and
 b) measuring the fluorescent signal.

In certain embodiments of the methods provided herein, the measuring step is performed in cell culture media.

The present disclosure also provides for the use of any of the compounds provided herein, any of the compositions provided herein, or any of the kits provided herein to assess cell viability.

IV. BRIEF DESCRIPTION OF THE FIGURES

Figure 3A:
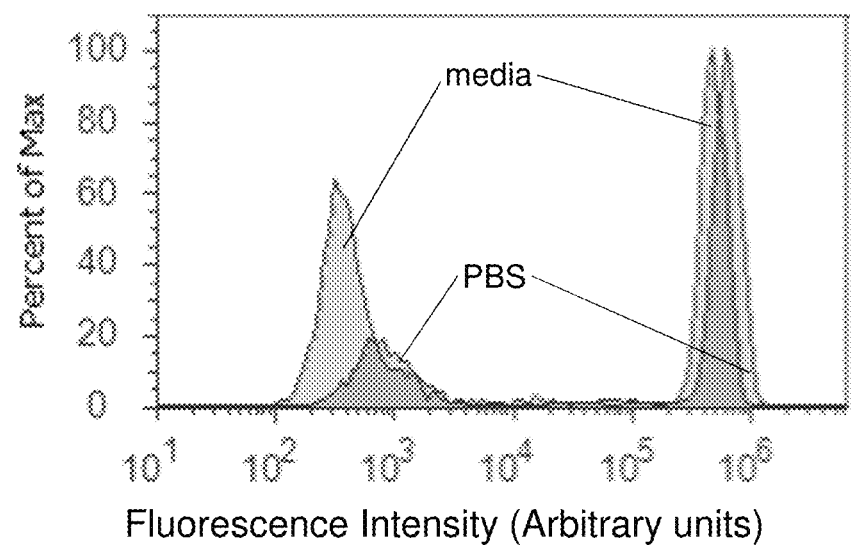

FIG. 3A shows results of staining fixed, permeabilized cells with Compound 4 in media and in PBS. The peaks for the two conditions mostly overlap, with the left peaks representing live cells and the right peaks representing dead cells. The PBS peaks were slightly to the right of the media peaks.

Figure 3B:
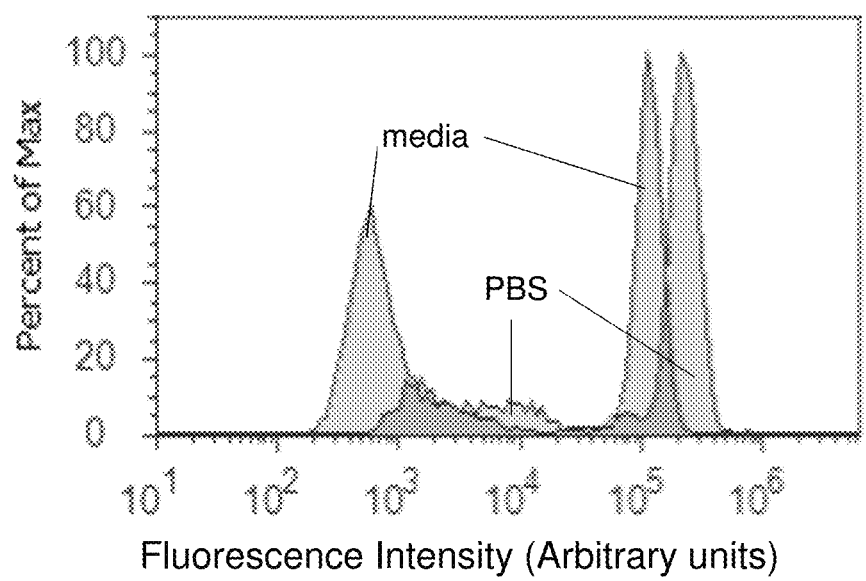

FIG. 3B shows results of staining fixed, permeabilized cells with Compound 2 in media and in PBS. The peaks for the two conditions mostly or partially overlap, with the left peaks representing live cells and the right peaks representing dead cells. The PBS peaks were slightly to the right of the media peaks.

Figure 4A:
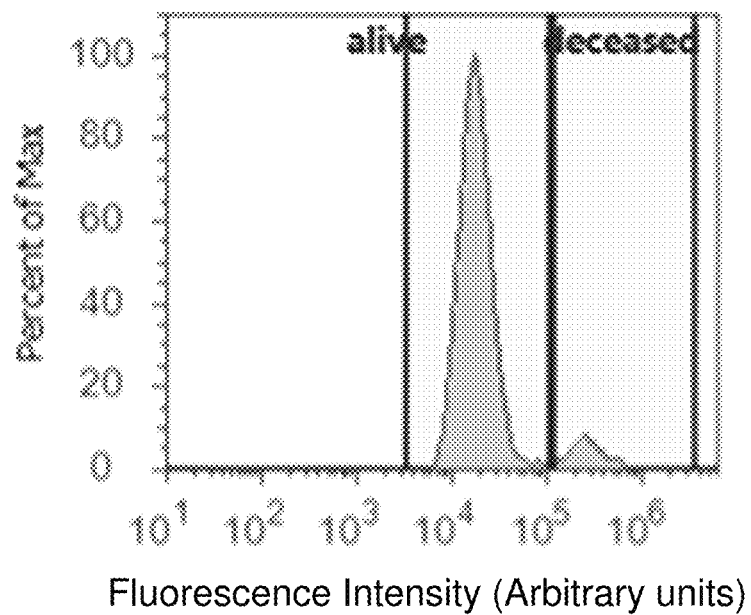
Figure 4B:
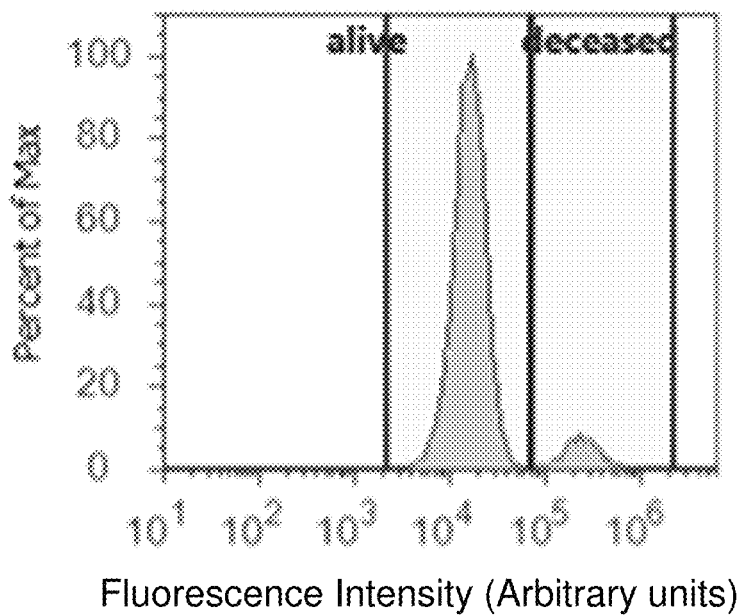

FIGS. 4A-B show cell viability results for untreated cells with Compound 1 in PBS (FIG. 4A) or complete media (FIG. 4B).

Figure 5A:
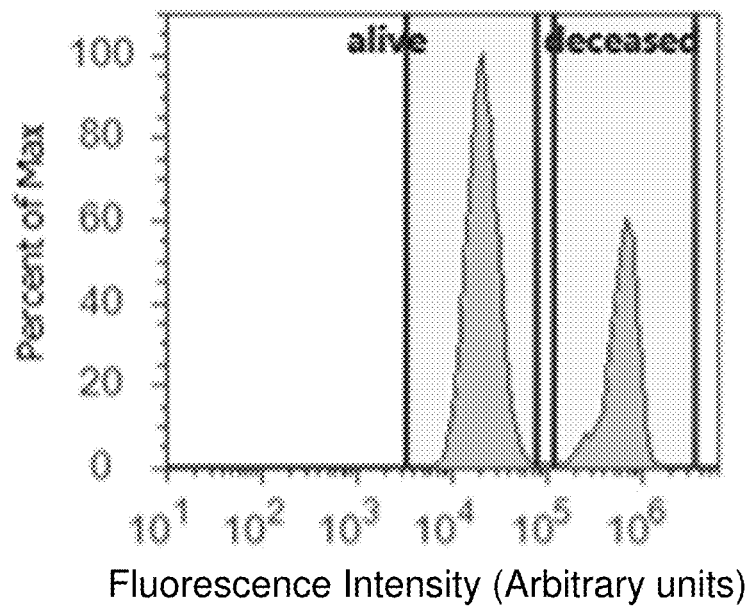
Figure 5B:
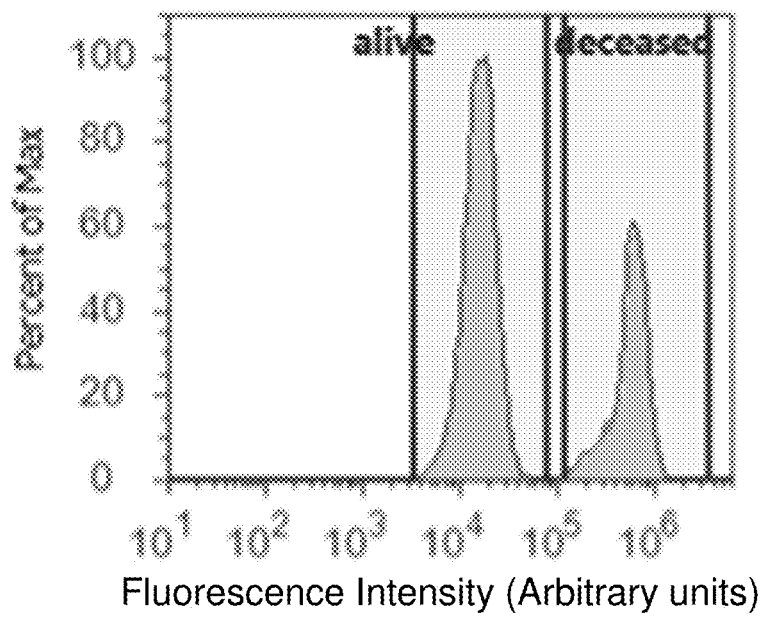

FIGS. 5A-B show cell viability results for a mixture of untreated and heat-killed cells with Compound 1 in PBS (FIG. 5A) or complete media (FIG. 5B).

Figure 6A:
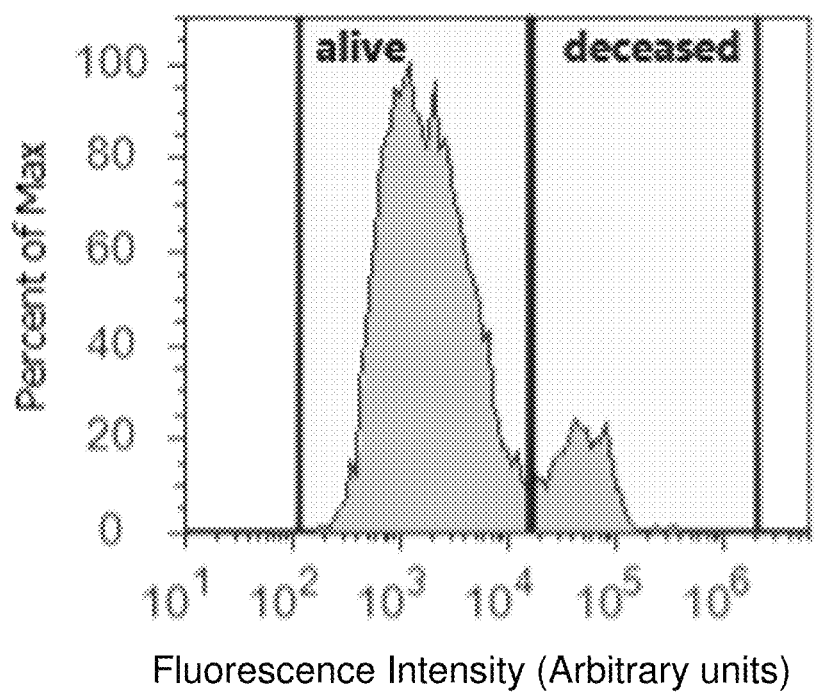
Figure 6B:
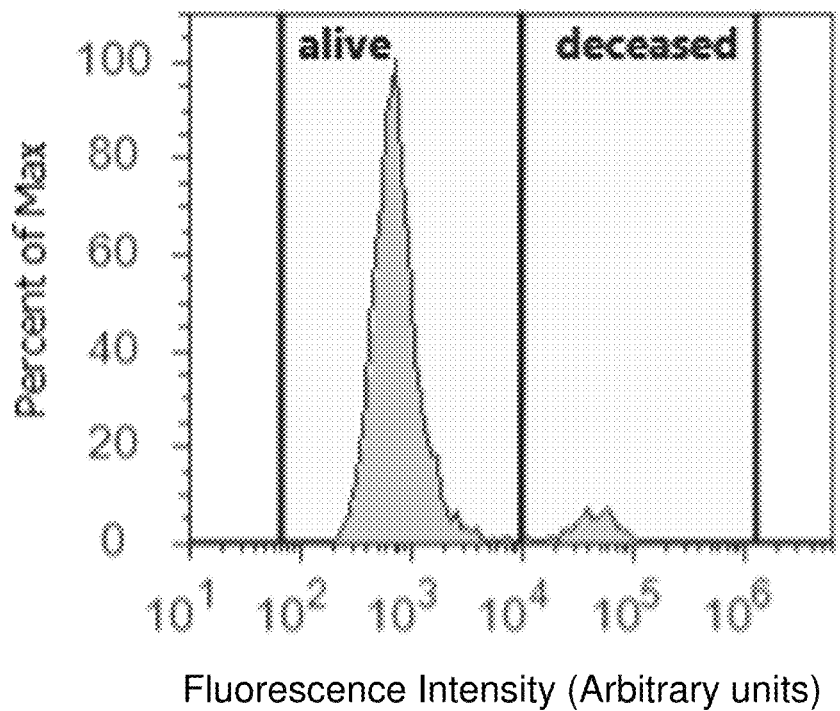

FIGS. 6A-B show cell viability results for fixed and permeabilized cells stained with Compound 1 in PBS (FIG. 6A) or complete media (FIG. 6B).

Figure 7A:
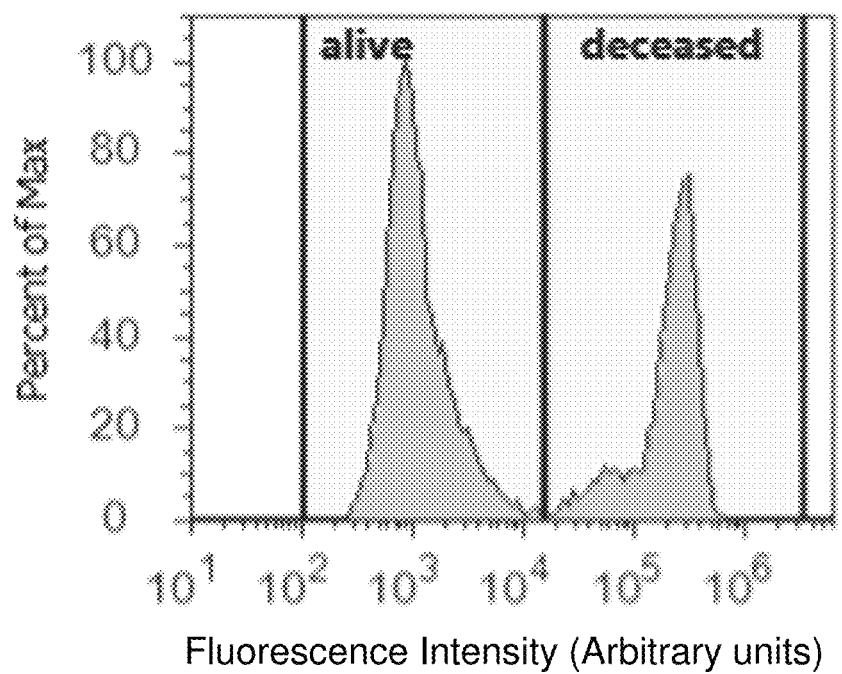
Figure 7B:
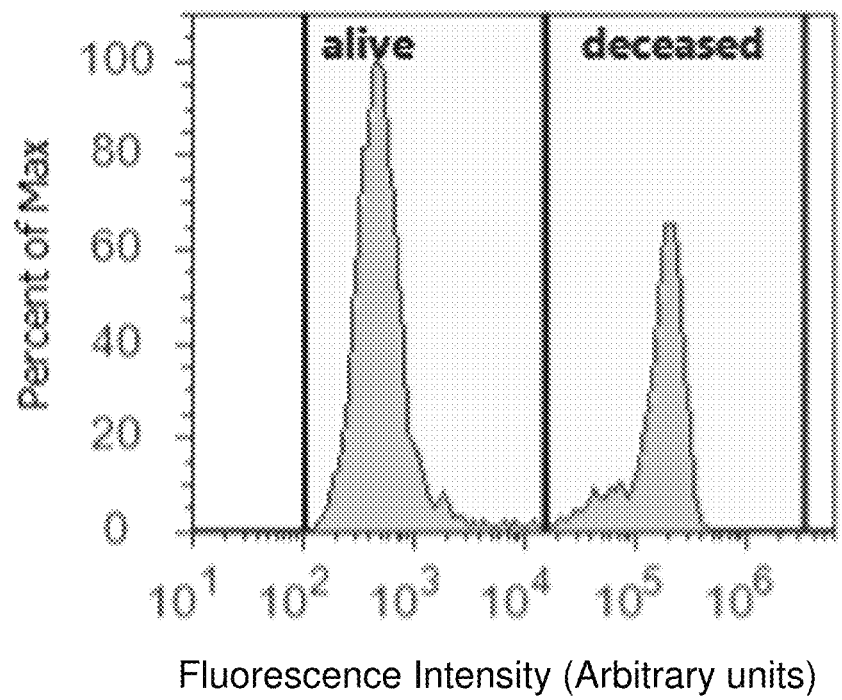

FIGS. 7A-B show cell viability results for a mixture of untreated and heat-killed cells fixed and permeabilized and then incubated with Compound 1 in PBS (FIG. 7A) or complete media (FIG. 7B).

Figure 8A:
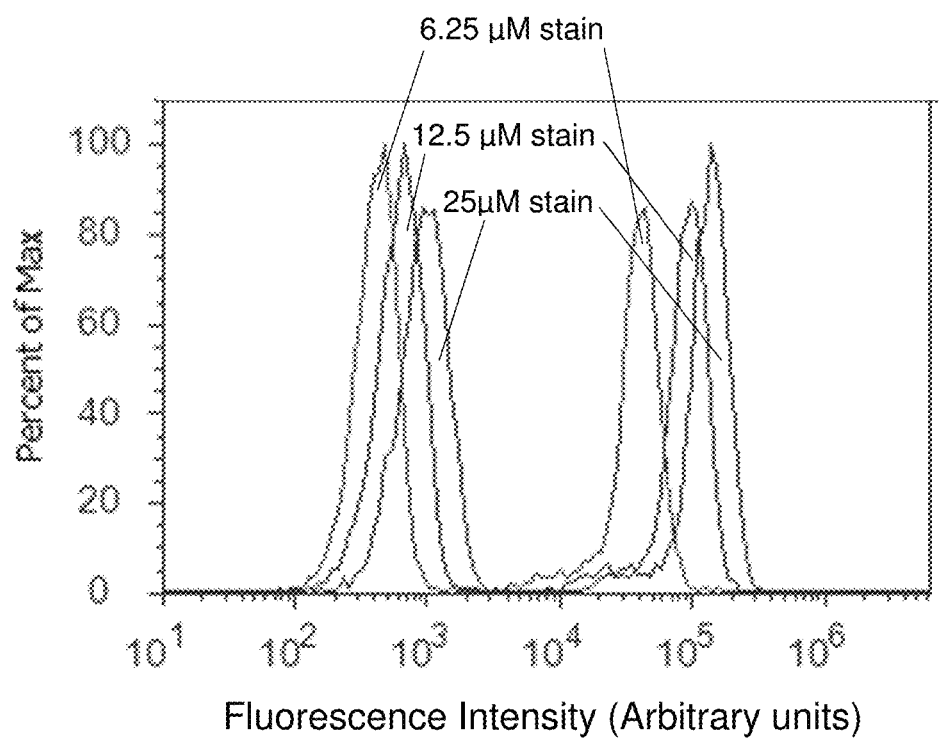
Figure 8B:
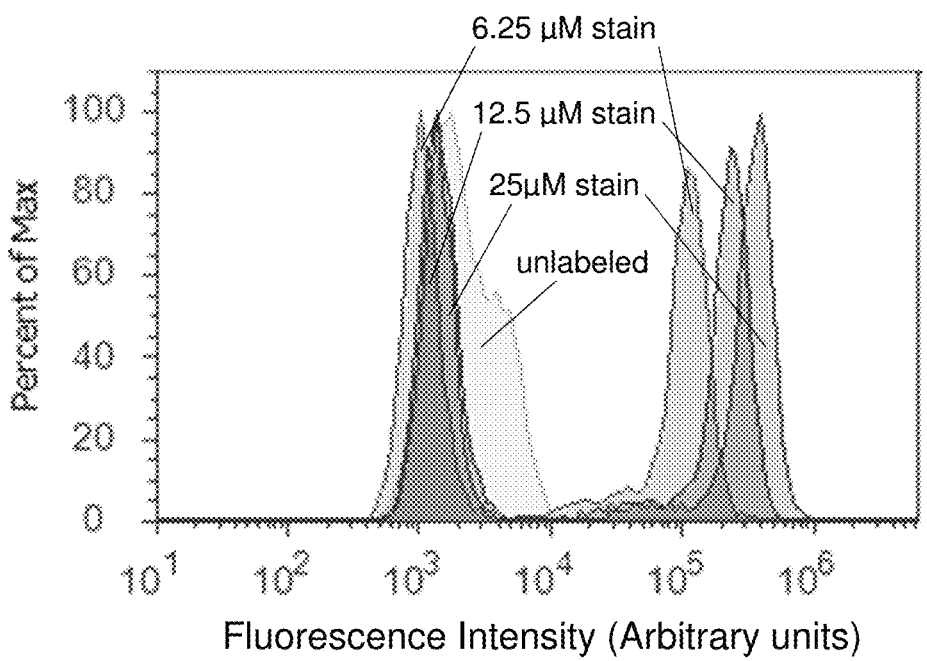

FIGS. 8A-B show cell viability results for a mixture of untreated and heat-killed cells incubated with Compound 4 at 6.25 µM, 12.5 µM, or 25 µM in complete media (FIG. 8A) or fixed and permeabilized and then incubated with Compound 4 in complete media (FIG. 8B). In FIG. 8A, the first and fourth peaks from the left are the 6.25 µM results; the second and fifth are the 12.5 µM results; and the third and sixth are the 25 µM results. The left three peaks in FIG. 8A represent live cells and the right three peaks represent dead cells. In FIG. 8B, the first and fifth peaks from the left are the 6.25 µM results; the second and sixth are the 12.5 µM results; and the third and seventh are the 25 µM results. The second and third peaks overlap almost entirely. The fourth peak is an unlabeled control. The left three peaks in FIG. 8B represent live labeled cells and the right three peaks represent dead cells.

Figure 9A:
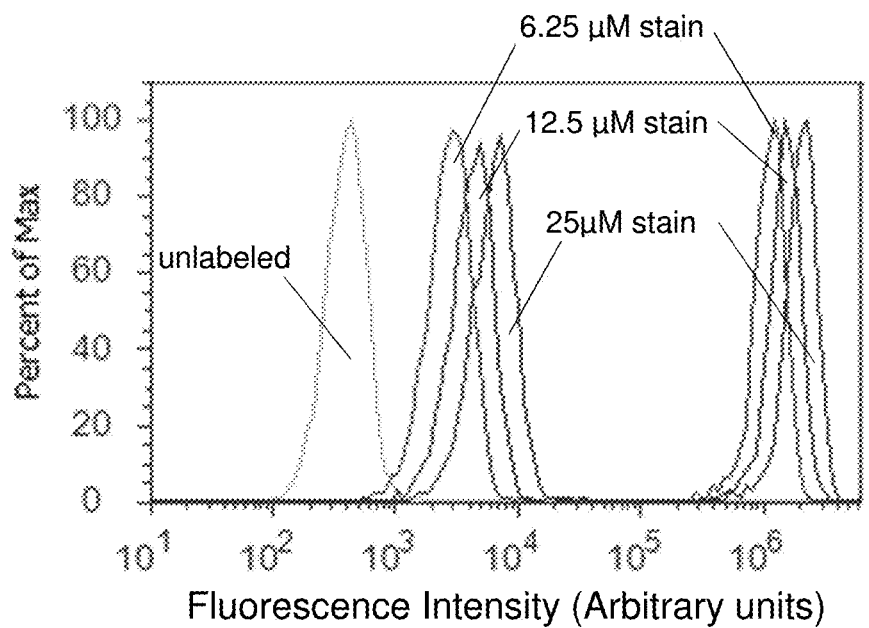
Figure 9B:
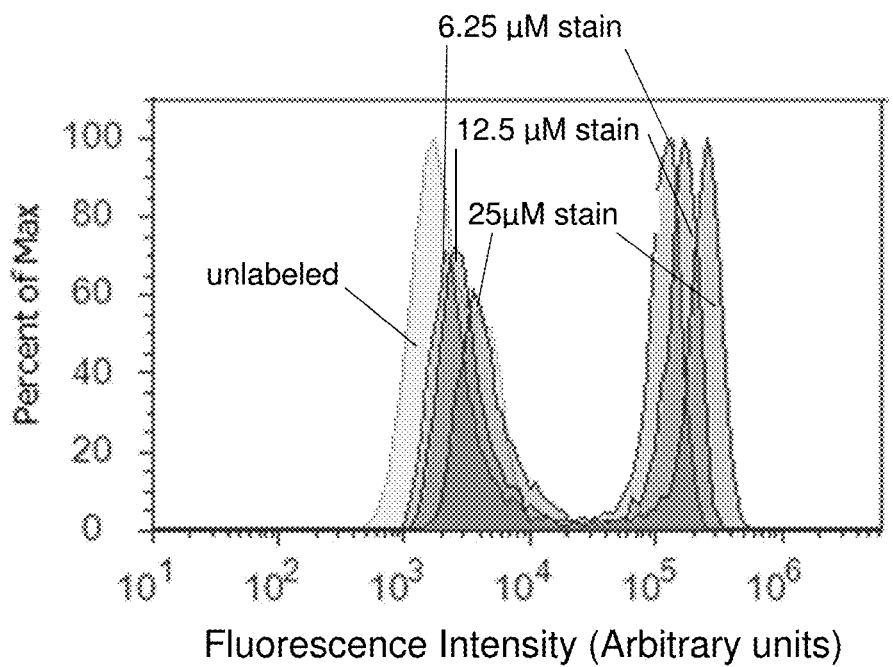

FIGS. 9A-B show cell viability results for a mixture of untreated and heat-killed cells incubated with Compound 2 at 6.25 µM, 12.5 µM, or 25 µM in complete media (FIG. 9A) or fixed and permeabilized and then incubated with Compound 2 in complete media (FIG. 9B). In FIG. 9A, the first peak from the left is an unlabeled control; the second and fifth peaks are the 6.25 µM results; the third and sixth are the 12.5 µM results; and the fourth and seventh are the 25 µM results. The left three peaks in FIG. 9A, excluding the unlabeled control, represent live cells and the right three peaks represent dead cells. The order of the peaks is the same in FIG. 9B, although the control and live cell peaks are more closely spaced.

Figure 10A:
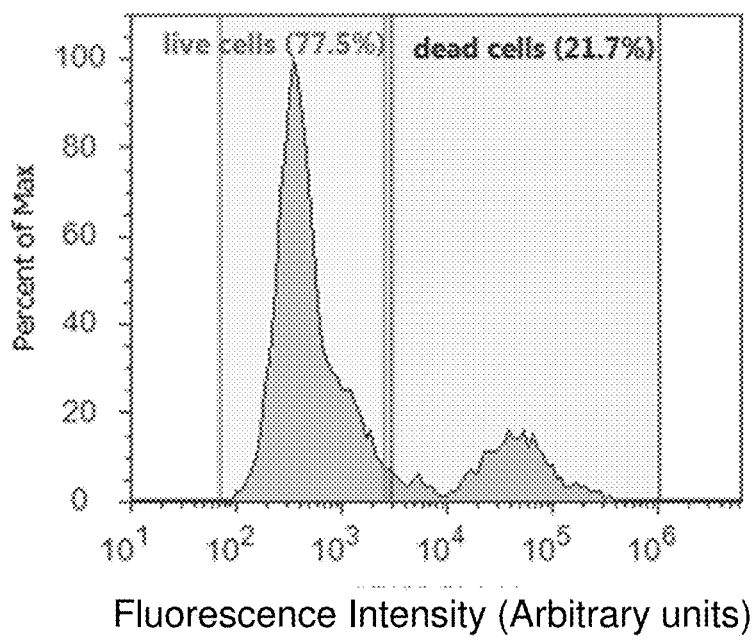
Figure 10B:
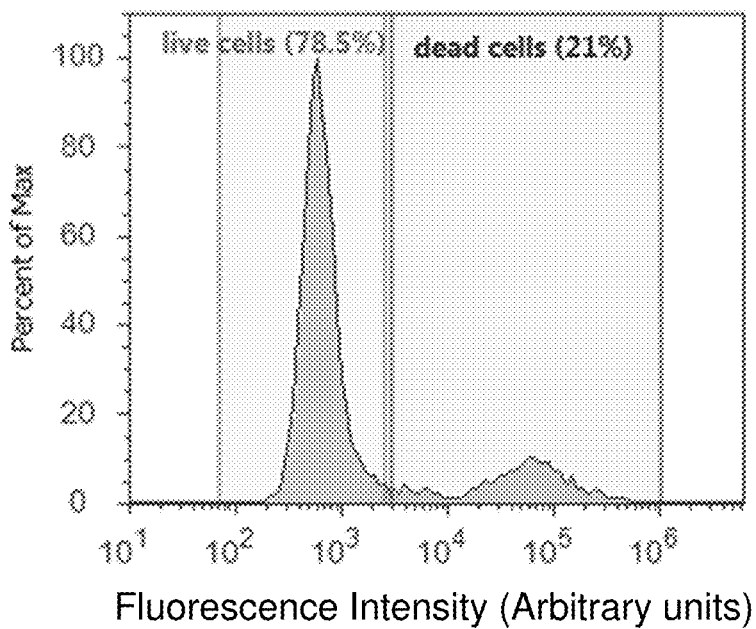
Figure 10C:
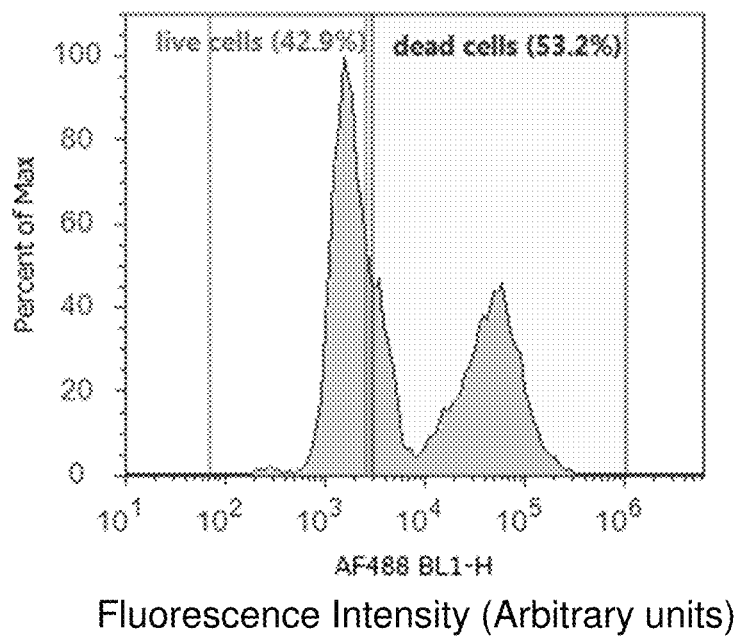
Figure 10D:
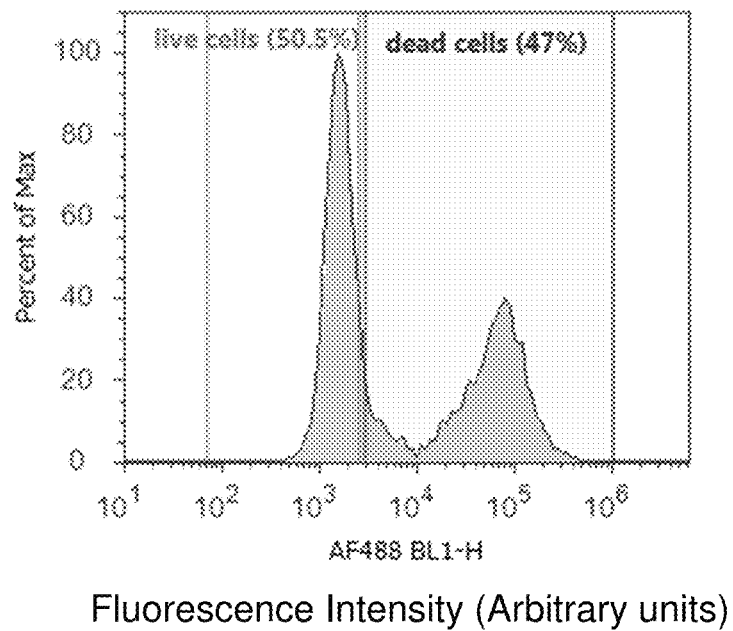
Figure 10E:
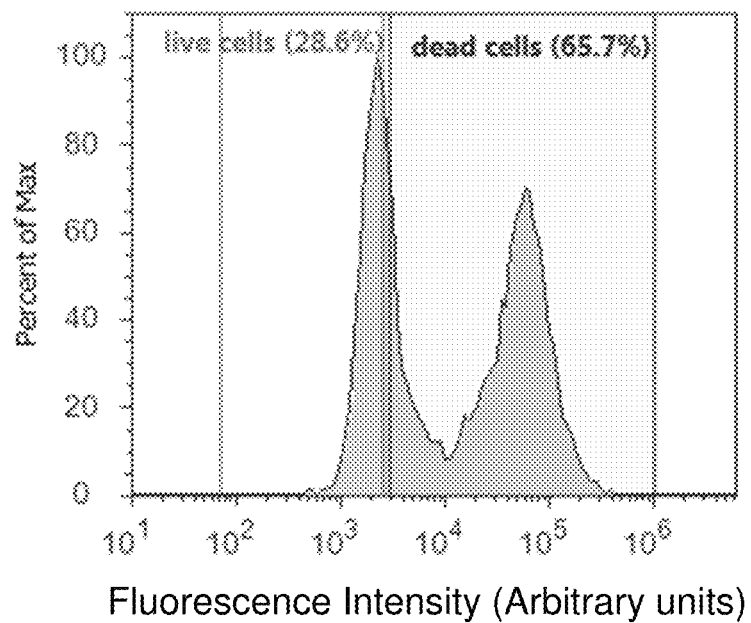
Figure 10F:
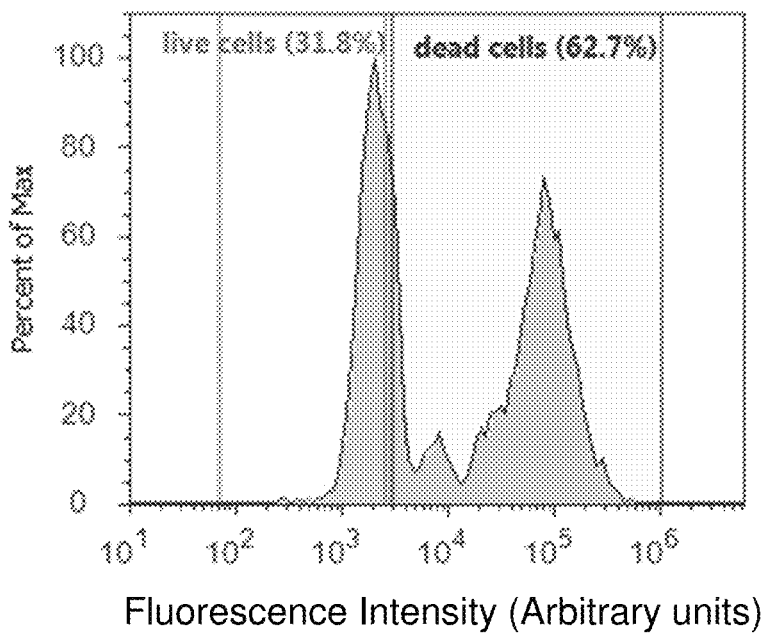

FIGS. 10A-F show cell viability results for untreated Ramos cells (FIGS. 10A-10B), Ramos cells treated with 10 µM camptothecin (FIGS. 10C-10D), or cells treated with 1 µM staurosporine (FIGS. 10E-10F); Compound 4 was used for staining in complete media. In FIGS. 10A, 10C and 10E, the cells were stained after fixation. In FIGS. 10B, 10D and 10F, the cells were stained after fixation and permeabilization.

V. DETAILED DESCRIPTION OF EMBODIMENTS OF THE DISCLOSURE

Reference will now be made in detail to certain embodiments of the disclosure, examples of which are illustrated in the accompanying drawings. While the present disclosure will be described in conjunction with the illustrated embodiments, it will be understood that they are not intended to limit the disclosure to those embodiments. On the contrary, this disclosure is intended to cover all alternatives, modifications, and equivalents, which may be included within the disclosure as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a dye" includes a plurality of dyes and reference to "a cell" includes a plurality of cells and the like.

Measured and measurable values are understood to be approximate, taking into account significant digits and the error associated with the measurement. All ranges are to be interpreted as encompassing the endpoints in the absence of express exclusions such as "not including the endpoints"; thus, for example, "within 10-15" includes the values 10 and 15. The use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings. Unless specifically noted in the specification, embodiments in the specification that recite "comprising" various components are also contemplated as "consisting of" or "consisting essentially of" the recited components.

The section headings used herein are for organizational purposes only and are not to be construed as limiting the desired subject matter in any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

A. Definitions

Unless stated otherwise, the following terms and phrases as used herein are intended to have the following meanings:

The term "or combinations thereof" as used herein refers to all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, colors and color channels such as near infrared, red, orange, yellow, green, cyan, blue, and violet have their ordinary and customary meaning in the arts of fluorescence detection in molecular and cell biology, including fluorescence microscopy and flow cytometry. Exemplary ranges for the colors and color channels are as follows: 380 nm to 435 or 440 nm for violet, 435 or 440 nm to 485 nm or 435 or 440 nm to 500 nm for blue, 485 to 500 nm or 500 nm to 520 nm for cyan, 500 nm or 520 nm to 560 nm or 500 nm or 520 nm to 565 nm for green, 560 or 565 nm to 590 nm or 560 or 565 nm to 600 nm for yellow, 590 nm or 600 nm to 625 nm or 590 nm or 600 nm to 650 nm for orange, 625 nm or 650 nm to 700 nm or 625 nm or 650 nm to 740 nm for red, and 700 nm or 740 nm to 1000 nm or 700 nm or 740 nm to 2000 nm for near infrared.

As used herein, the term "kit" refers to a packaged set of related components, such as one or more compounds or compositions disclosed herein and one or more related materials such as solvents, solutions, buffers, instructions, desiccants, or cells.

The terms "linker" and "linkage" are used interchangeably and mean a chemical moiety comprising a covalent bond or a chain of atoms that covalently attaches (or is attached to) two moieties, e.g., a fluorescent moiety and a reactive moiety.

"Linking moiety" means a chemically reactive group, substituent or moiety, e.g. a nucleophile or electrophile, capable of reacting with another molecule to form a linkage by a covalent bond.

"Substituted" as used herein refers to a molecule wherein one or more hydrogen atoms are replaced with one or more non-hydrogen atoms, functional groups or moieties. By example, an unsubstituted nitrogen is —$NH_2$, while a substituted nitrogen is —$NHCH_3$. Exemplary substituents include but are not limited to halogen, e.g., fluorine and chlorine, ($C_1$-$C_8$) alkyl, sulfate, sulfonate, sulfone, amino, ammonium, amido, nitrile, nitro, lower alkoxy, phenoxy, aromatic, phenyl, polycyclic aromatic, heterocycle, water-solubilizing group, linkage, and linking moiety.

"Alkyl" means a saturated or unsaturated, branched, straight-chain, branched, or cyclic hydrocarbon radical derived by the removal of one hydrogen atom from a single carbon atom of a parent alkane, alkene, or alkyne. Typical alkyl groups contain 1 to 12 saturated and/or unsaturated carbons, including, but not limited to, methyl, ethyl, propyl, butyl, and the like. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Aryl" or "Ar" refers to an aromatic carboxylic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that at least one point of attachment is at an aromatic carbon atom. In some embodiments, an aryl group is phenyl or naphthyl.

"Heterocycle" means any ring system having at least one non-carbon atom in a ring, e.g. nitrogen, oxygen, and sulfur. Heterocycles include, but are not limited to: azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, pyrrolidine, furan, benzofuran, thiophene, benzothiophene, 2-pyridyl, 3-pyridyl, 4-pyridyl, 2-quinolyl, 3-quinolyl, 4-quinolyl, 2-imidazole, 4-imidazole, 3-pyrazole, 4-pyrazole, pyridazine, pyrimidine, pyrazine, cinnoline, pthalazine, quinazoline, quinoxaline, 3-(1,2,4-N)-triazolyl, 5-(1,2,4-N)-triazolyl, 5-tetrazolyl, 4-(1-O, 3-N)-oxazole, 5-(1-O, 3-N)-oxazole, 4-(1-S, 3-N)-thiazole, 5-(1-S, 3-N)-thiazole, 2-benzoxazole, 2-benzothiazole, 4-(1,2,3-N)-benzotriazole, benzimidazole, and tetrahydrofuranyl. A "heteroaryl" is an aromatic heterocycle. A "heterocycloalkyl" is a non-aromatic heterocycle.

"Substituted alkyl", "substituted aryl," "substituted heterocycle," "substituted heteroaryl," and "substituted heterocycloalkyl" mean alkyl, aryl, heterocycle, heteroaryl, and heterocycloalkyl, respectively, in which one or more hydrogen atoms are each independently replaced with another substituent. Typical substituents include, but are not limited to, —X, —R, —OH, —OR, —SR, —SH, —$NH_2$, —NHR, —$NR_2$, —$^+NR_3$, —N=$NR_2$, —$CX_3$, —CN, —OCN, —SCN,
—NCO, —NCS, —NO, —$NO_2$, —$N_2^+$, —$N_3$, —NHC(O)R, —C(O)R, —C(O)$NR_2$, —S(O)$_2$O$^-$, —S(O)$_2$R, —OS(O)$_{20}$R, —OS(O)$_{20}$R, —S(O)$_2$NR, —S(O)R, —OP(O)(OR)$_2$, —P(O)(OR)$_2$, —P(O)(O$^-$)$_2$, —P(O)(OH)$_2$, —C(O)R, —C(O)X, —C(S)R, —C(O)OR, —$CO_2$, —C(S)OR, —C(O)SR, —C(S)SR, —C(O)$NR_2$, —C(S)$NR_2$, —C(NR)$NR_2$, where each X is independently a halogen and each R is independently —H, $C_1$-$C_6$ alkyl, $C_5$-$C_{14}$ aryl, heterocycle, or linking group. In some embodiments, 1 to 5, particularly 1 to 3, or more particularly 1 to 2 substituents are present, which can be one or more of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxylalkyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein. In general, reference to a "ring" includes substituted rings as well as unsubstituted rings unless the context dictates otherwise.

"Water-solubilizing group" means a substituent which increases the solubility of the compounds of the disclosure in aqueous solution. Exemplary water-solubilizing groups include but are not limited to quaternary amine, sulfate, sulfonate, carboxylate, phosphonate, phosphate, polyether, polyhydroxyl, and boronate.

Unless indicated otherwise, the nomenclature of substituents that are not explicitly defined herein are arrived at by naming the terminal portion of the functionality followed by the adjacent functionality toward the point of attachment. For example, the substituent "arylalkylcarbonyl" refers to the group (aryl)-(alkyl)-C(O)—.

It is understood that in all substituted groups defined herein, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to -substituted aryl-(substituted aryl)-substituted aryl.

Similarly, it is understood that the definitions provided herein are not intended to include impermissible substitution patterns (e.g., methyl substituted with 5 fluoro groups).

The compounds disclosed herein may exist in unsolvated forms as well as solvated forms, including hydrated forms. These compounds may exist in multiple crystalline or amorphous forms. In general, all physical forms are equivalent for the uses described herein and are intended to be within the scope of the present disclosure. The compounds disclosed herein may possess asymmetric carbon atoms (i.e., chiral centers) or double bonds; the racemates, diastereomers, geometric isomers and individual isomers of the compounds described herein are within the scope of the present disclosure. The compounds described herein may be prepared as a single isomer or as a mixture of isomers.

Where substituent groups are specified by their conventional chemical formulae and are written from left to right, they equally encompass the chemically identical substituents, which would result from writing the structure from right to left, e.g., —$CH_2O$— is intended to also recite —$OCH_2$—.

It will be understood that the chemical structures that are used to define the compounds disclosed herein are each representations of one of the possible resonance structures by which each given structure can be represented. Further, it will be understood that by definition, resonance structures are merely a graphical representation used by those of skill in the art to represent electron delocalization, and that the present disclosure is not limited in any way by showing one particular resonance structure for any given structure.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

"Amino" refers to the group —$NH_2$.

"Substituted amino" refers to the group —NR'R" where R' and R" are independently selected from hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, —$SO_2$-alkyl, —$SO_2$-substituted alkyl, —$SO_2$-alkenyl, —$SO_2$-substituted alkenyl, —$SO_2$-cycloalkyl, —$SO_2$-substituted cycloalkyl, —$SO_2$-cycloalkenyl, —$SO_2$-substituted cylcoalkenyl, —$SO_2$-aryl, —$SO_2$-substituted aryl, —$SO_2$-heteroaryl, —$SO_2$-substituted heteroaryl, —$SO_2$-heterocyclic, and —$SO_2$-substituted heterocyclic and wherein R' and R" are optionally joined, together with the nitrogen bound thereto to form a heterocyclic or substituted heterocyclic group, provided that R' and R" are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" are hydrogen.

"Amide" refers to the group —NH—C(O)—. "Substituted amide" refers to the group —NR'—C(O)— where R' is selected from alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where R' and R" are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"H" indicates hydrogen.

"Halo" or "halogen" refers to fluoro, chloro, bromo and iodo.

"Hydroxy" or "hydroxyl" refers to the group —OH.

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal.

As used herein, a "pharmaceutically acceptable" or "biologically compatible" counterion is a counterion that is not toxic as used, and does not have a substantially deleterious effect on biomolecules. A pharmaceutically acceptable or biologically compatible salt comprises a pharmaceutically acceptable or biologically compatible counterion. Examples of such counterions include, among others, $K^+$, $Na^+$, $Cs^+$, $Li^+$, $Ca^{2+}$, $Mg^{2+}$, $Cl^-$, $AcO^-$, and alkylammonium or alkoxyammonium salts. Where compounds bearing a non-zero charge are shown, the presence of pharmaceutically acceptable or biologically compatible counterions is implied, either as a solid or in solution, to provide overall charge neutrality.

The term "linker" or "L", as used herein, refers to a single covalent bond or a moiety comprising a series of stable covalent bonds, the moiety often incorporating 1-40 plural valent atoms selected from the group consisting of C, N, O, S and P that covalently attach the fluorogenic or fluorescent compounds to another moiety such as a chemically reactive group or a biological and non-biological component. The number of plural valent atoms in a linker may be, for example, 0, 1, 2, 3, 4, 5, 6, 7, 8, 9, 10, 20, 25, 30 or a larger number up to 40 or more. A linker may be linear or non-linear; some linkers have pendant side chains or pendant functional groups, or both. Examples of such pendant moieties are hydrophilicity modifiers, for example solubilizing groups like, e.g. sulfo (—$SO_3H$ or —$SO_3^-$). In certain embodiments, L is composed of any combination of single, double, triple or aromatic carbon-carbon bonds, carbon-nitrogen bonds, nitrogen-nitrogen bonds, carbon-oxygen bonds and carbon-sulfur bonds. Exemplary linking members include a moiety that includes —C(O)NH—, —C(O)O—, —NH—, —S—, —O—, and the like. Linkers may, by way of example, consist of a combination of moieties selected from alkyl, —C(O)NH—, —C(O)O—, —NH—, —S—, —O—, C(O)—, —S(O)$_n$— where n is 0, 1 or 2, —O—, 5- or 6-membered monocyclic rings, and optional pendant functional groups, for example sulfo, hydroxy and carboxy. The moiety formed by a linker bonded to a reactive group ($R_x$) may be designated -L-$R_x$. The reactive group may be reacted with a substance reactive therewith, whereby the linker becomes bonded to a conjugated substance ($S_c$) and may be designated -L-$S_c$, or in some cases, the linker may contain a residue of a reactive group (e.g. the carbonyl group of an ester) and may be designated "-$L_R$".

The term "reactive group" (or "$R_x$"), as used herein, refers to a group that is capable of reacting with another chemical group to form a covalent bond, i.e., is covalently reactive under suitable reaction conditions, and generally represents a point of attachment for another substance. The reactive group is a moiety, such as carboxylic acid or succinimidyl ester, on the compounds of the present disclosure that is capable of chemically reacting with a functional group on a different compound to form a covalent linkage. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides, succinimidyl esters (SE), sulfodichlorophenyl (SDP) esters, sulfotetrafluorophenyl (STP) esters, tetrafluorophenyl (TFP) esters, pentafluorophenyl (PFP) esters, nitrilotriacetic acids (NTA), aminodextrans, cyclooctyne-amines and the like. Methods to prepare each of these functional groups are well known in the art and their application to or modification for a particular purpose is within the ability of one of skill in the art (see, for example, Sandler and Karo, eds., *Organic Functional Group Preparations*, Academic Press, San Diego, 1989).

"Or" is used in the inclusive sense, i.e., equivalent to "and/or," unless the context requires otherwise.

B. Exemplary Compounds, Compositions, Kits, Methods, and Uses

Provided herein are compounds that can be used to evaluate viability of cells by flow cytometry. Advantageously, these compounds can be used with cells in complete media and result in a reduction of staining time compared with current flow cytometry live/dead reagents which are live cell impermeable and reactive with protein —$NH_2$ groups. Reagents that are currently available require removal of proteins prior to staining with staining times of up to 30 minutes. In contrast, the compounds of the present disclosure are reactive with double-stranded DNA (dsDNA) and are based on cis-platin and N-mustard analogs. These are two of a very small set of reactivities selective for cellular dsDNA over cellular proteins and other molecules. Advantageously, by changing the probe reactivity from protein to DNA the compounds of the present disclosure can be used in complete media without interference by protein components and other aliphatic amines typically present, such as TRIS and serum proteins. A significant reduction in the staining time (and therefore a reduction in the duration of the workflow) was an unexpected advantage resulting from the compounds' selectivity of dsDNA.

In some embodiments, a compound of Formula I is provided:

D-L-R (Formula I)

wherein D is a fluorescent moiety, L is a linker (which can be a bond or a chain, discussed in detail below), and R is Formula IA or Formula IB, both discussed in detail below. The compounds can be useful, e.g., for differentially staining dead cells in that the compounds can cross the membrane of dead cells and react with intracellular contents, e.g., nucleic acids, through R. Thus, the fluorescent moiety becomes stably associated with the intracellular contents of dead cells, and dead cells can be distinguished from live cells on the basis of a greater degree of fluorescence.

In some embodiments, R is Formula IA:

—B—N($R^1$)($R^2$) (Formula IA)

wherein B is an aliphatic group, a bond or an aromatic group, including but not limited to an aryl, substituted aryl, heteroaryl, or substituted heteroaryl; and $R^1$ and $R^2$ are each independently ethyl substituted with a Z at the 2 position or substituted ethyl further substituted with a Z at the 2 position, and each Z is independently OH, Cl, Br, I, or

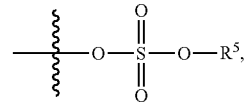

where $R^5$ is alkyl, substituted alkyl, aryl or substituted aryl.

In some embodiments, R is

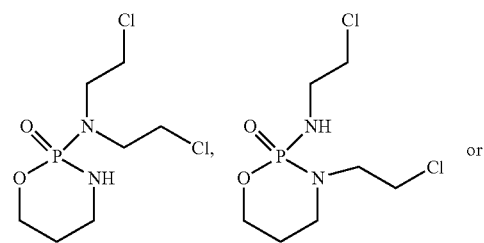

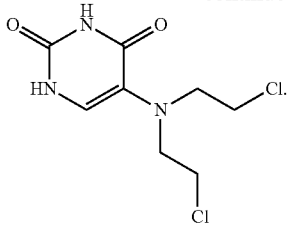

Formula IA is related to nitrogen mustard compounds, which can comprise bis(2-chloroethyl)amino functionality and are nucleic acid alkylating agents believed to form an aziridinium ring (three-membered heterocycle with one nitrogen) intermediate that reacts with N7 of guanine to form a covalent adduct. In double-stranded nucleic acids, a 5'-GC or 5'-GNC sequence has been reported to form an interstrand crosslink with nitrogen mustard compounds.

The Z in $R^1$ and $R^2$ of Formula IA is a leaving group that can undergo displacement to form an aziridinium ring intermediate. In nitrogen mustards, Z is Cl, but other leaving groups such as OH, Br, or I can be used in some embodiments. To allow for formation of the aziridinium ring, it is separated from the nitrogen by two carbons; the 2 position to which Z is bonded becomes the electrophile attacked by the nitrogen during aziridinium ring formation.

In some embodiments, at least one of $R^1$ and $R^2$ is 2-chloroethyl. In some embodiments, at least one of $R^1$ and $R^2$ is 2-hydroxyethyl. In some embodiments, $R^1$ and $R^2$ are the same. In some embodiments, —N($R^1$)($R^2$) is

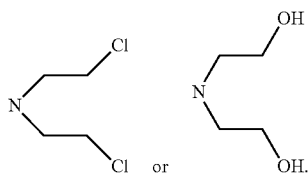 [SMILES: ClCCNCCCl ; OCCNCCO]

In certain embodiments, B in Formula IA can be an aryl, substituted aryl, heteroaryl, or substituted heteroaryl, such as phenyl, pyridinyl, or substituted versions thereof. In some embodiments, B is a six-membered ring. In some embodiments, B does not comprise more than one heteroatom. B in Formula IA is situated between L and —N($R^1$)($R^2$); in some embodiments, L is para to —N($R^1$)($R^2$), i.e., L and —N($R^1$)($R^2$) are diametrically opposed across the B ring or ring system.

In some embodiments, R is

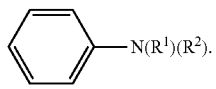

In some embodiments, R is

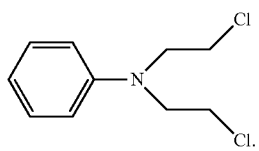 [SMILES: ClCCN(CCCl)c1ccccc1]

In some embodiments, R is

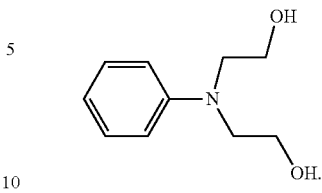

In some embodiments, R is Formula IB:

-A-Pt(X)($R^3$)($R^4$)        (Formula IB)

which comprises a platinum (Pt) complex with square planar geometry. The platinum is believed to be capable of bonding to nucleic acids in a reaction involving displacement of X, which may be similar to the mechanism by which certain platinum-based chemotherapeutics, such as cisplatin, become associated with nucleic acids. In some embodiments, X is Cl, Br, or I. In some embodiments, X is Cl.

In Formula IB, A is a heterocycloalkyl or substituted heterocycloalkyl in which a nitrogen is bonded to the platinum. In some embodiments, there are one, two, or three nitrogens in A. In some embodiments, A comprises at least two nitrogens. When two or more nitrogens are present, one can be bonded to the linker L and another can be bonded to Pt. In some embodiments, the bond to Pt and the bond to L are not adjacent in ring A. In some embodiments, the bond to Pt and the bond to L are diametrically opposed in ring A. In some embodiments, A is a five-, six-, or seven-membered ring, e.g., a six-membered ring. In some embodiments, at least one, two, three, four, or all carbons in ring A are unsubstituted. In some embodiments, A is

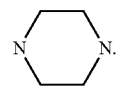

In some embodiments, $R^3$ and $R^4$ are each independently —NH$_2$$R^6$, wherein $R^6$ is H, $C_{1-6}$ alkyl, or substituted $C_{1-6}$ alkyl. In some embodiments, $R^6$ is H. In some embodiments, $R^6$ is $C_{1-3}$ alkyl. In some embodiments, $R^6$ is methyl. In some embodiments, $R^6$ is ethyl.

In some embodiments, $R^3$ and $R^4$, together with the platinum of Formula IB, form a ring in which the two atoms bonded to the platinum are nitrogen and the ring comprises at least two carbons between the nitrogens. In some embodiments, the nitrogens in the ring are unsubstituted. In some embodiments, the carbons in the ring are unsubstituted. In some embodiments, the ring is a five-, six-, or seven-membered ring, e.g., a five-membered ring. In some embodiments, the ring is a six-membered ring. In some embodiments, there are not more than three carbons between the nitrogens in the ring, such as not more than two carbons between the nitrogens. In some embodiments, the ring is

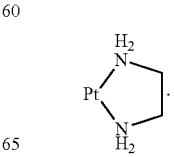

In some embodiments, the ring formed by $R^3$, $R^4$, and the platinum of Formula IB comprises $L^2$ between the nitrogens bound to the platinum. $L^2$ can be an alkylene or a substituted alkylene, such as a $C_{1-3}$ alkylene or substituted $C_{1-3}$ alkylene; a methylene, ethylene, or propylene; or an ethylene or substituted ethylene. In some embodiments, $L^2$ is an ethylene.

In some embodiments, R is

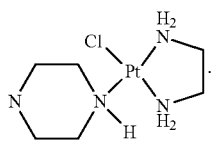

The linker L serves to connect R to the fluorescent moiety D. In some embodiments, L is a bond.

Rigid and non-rigid linkers may be useful. Generally, the linkage linking D to R should not (i) inhibit reactivity of R or (ii) adversely affect the properties of the label, e.g. quenching or bleaching fluorescence of the fluorescent moiety. D and R can be attached to L at sites including an amino or carboxy group. Peptides can be functionalized to bear reactive amino, thiol, sulfide, disulfide, hydroxyl, and carboxyl groups at any of these sites. L may be any bond, such as an amide or phosphate, or comprise a chain, such as an alkyldiyl, phenyldiyl, or benzydiyl, and substituted forms thereof.

In some embodiments, L is a chain, such as a 1-15 atom chain or a 6-13 atom chain. L can comprise an amide. Chain length includes only on-pathway atoms and not branched atoms; for example, the amide-containing chain —$CH_2$—C(O)—NH—$CH_2$— is considered a 4-atom chain because the amide oxygen and the protons are not on-pathway. In some embodiments, L comprises a nitrogen that is bonded to D, which can be but is not necessarily part of an amide; for example, the nitrogen can be bonded to a carbonyl carbon in D, thereby forming an amide. In some embodiments, the nitrogen bonded to D is linked to an internal amide in L by an alkylene chain, such as a propylene, butylene, pentylene, hexylene, or substituted $C_{3-6}$ alkylene. In some embodiments, such an alkylene chain is bonded to the nitrogen of the internal amide. In some embodiments, when an internal amide is present, it is linked to R by an alkylene chain, such as a methylene, ethylene, propylene, butylene, or substituted $C_{1-4}$ alkylene, which can be bonded to the carbonyl carbon of the internal amide. Exemplary linkers include (11-membered chain)

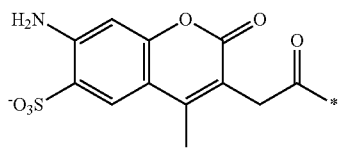

and (10-membered chain)

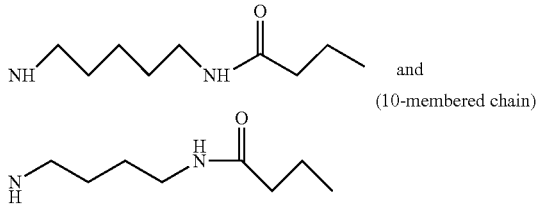

which can be attached, e.g., to D at the leftmost nitrogen and to R at the rightmost carbon.

In further embodiments, L is —N($R_{N1}$)—[$CH_2$]$_n$—, wherein n ranges from 1 to 10 and $R_{N1}$ is H or optionally substituted $C_{1-6}$ alkyl. In some embodiments, L is —N($R_{N1}$)-$L_a$-, wherein $L_a$ is a $C_{2-10}$ alkylene optionally interrupted by one or both of —N($R_{N1}$)—C(O)— or —$N^+(R_{N2})_2$—, wherein each $R_{N1}$ is independently H or optionally substituted $C_{1-6}$ alkyl and each $R_{N2}$ is independently an optionally substituted $C_{1-6}$ alkyl. In some embodiments, L is —C(O)—[$CH_2$]$_n$—, wherein n ranges from 1 to 10. In some embodiments, L is —N($R_{N1}$)—[$CH_2$]$_n$—C(O)—, wherein n ranges from 1 to 10 and $R_{N1}$ is H or optionally substituted $C_{1-6}$ alkyl. In some embodiments, L is [$CH_2$]$_n$—C(O)—, wherein n ranges from 1 to 10. In some embodiments, L is —[$CH_2$]$_n$—$N^+(R_{N2})_2$—[$CH_2$]$_n$—, wherein each $R_{N2}$ is independently an optionally substituted $C_{1-6}$ alkyl. In any of the foregoing, n can be 1, 2, 3, 4, 5, 6, 7, 8, 9, or 10. In any of the foregoing, the optionally substituted $C_{1-6}$ alkyl can be a methyl, ethyl, $C_3$ alkyl, $C_4$ alkyl, $C_5$ alkyl, or $C_6$ alkyl, any of which can be optionally substituted. In some embodiments, each $R_{N2}$ is methyl. In some embodiments, each $R_{N1}$ is methyl. In some embodiments, each $R_{N1}$ is H. In some embodiments, L is —NH—[$CH_2$]$_2$—. In some embodiments, L is —NH—[$CH_2$]$_4$—. In some embodiments, L is —NH—[$CH_2$]$_5$—. In some embodiments, L is —NH—[$CH_2$]$_2$—NH—C(O)—$CH_2$—N($CH_3$)$_2$—[$CH_2$]$_2$—.

D is a fluorescent moiety. In some embodiments, D is chosen such that the compound has a near infrared, red, orange, yellow, green, cyan, blue, or violet emission maximum. Exemplary fluorescent moieties include those in the Alexa Fluor® series, such as Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, or Alexa Fluor® 790. Exemplary fluorescent moieties are shown below, where the asterisk indicates an exemplary point of attachment to L (i.e., the carbonyl carbon adjacent to the asterisk in the structures below is considered the terminal atom of D, and what is bonded to it is considered part of L, which may be a nitrogen that forms an amide as discussed above). In some embodiments, D is chosen from the compounds listed below:

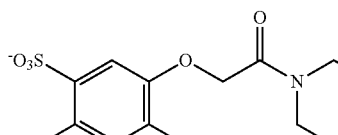

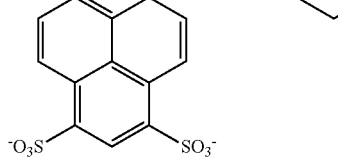

23
-continued
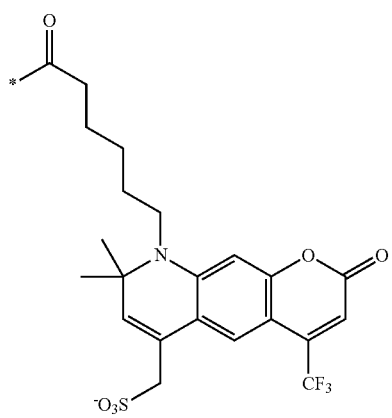
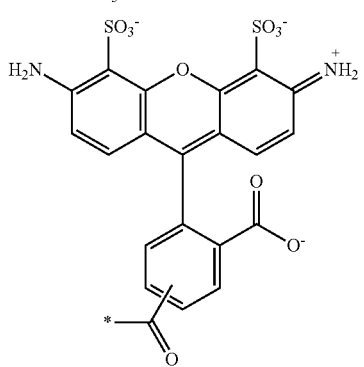
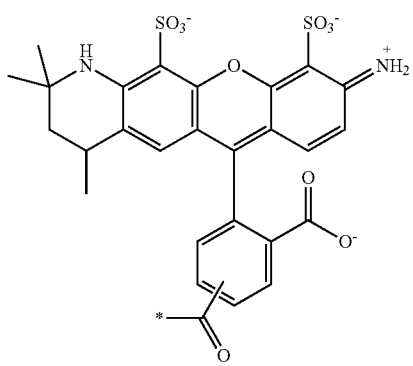
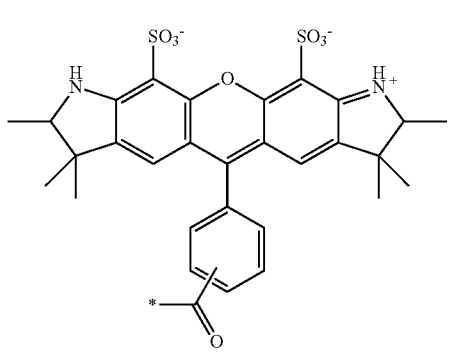
24
-continued
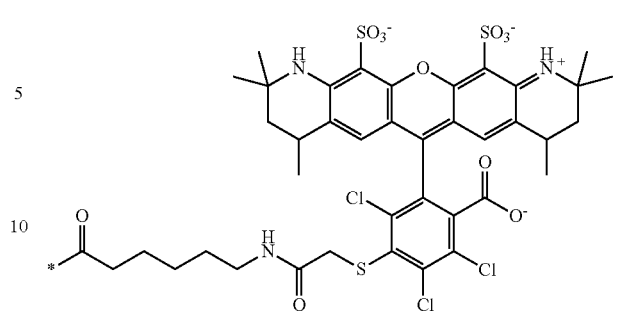
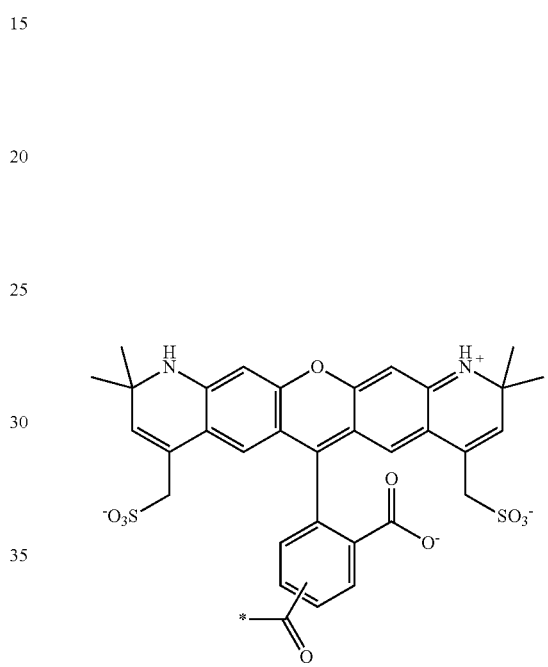
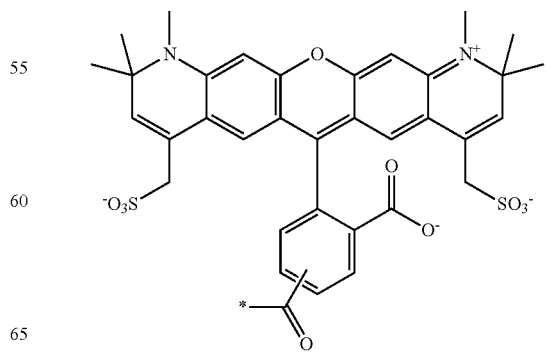

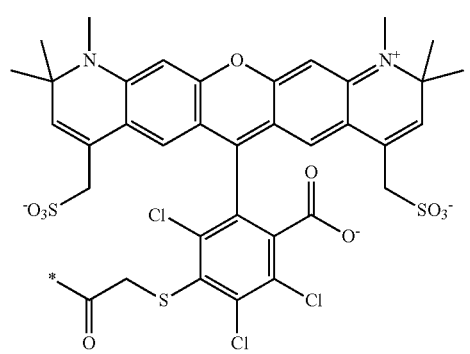

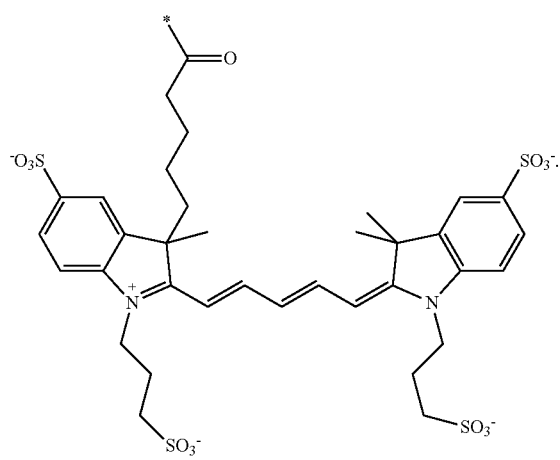

Other exemplary fluorescent moieties that can be incorporated into compounds according to the disclosure include a xanthene dye, a cyanine dye, a phenanthridinium dye, a bisbenzimide dye, a bisbenzimidazole dye, an acridine dye, a chromomycinone dye, OliGreen™ (Thermo Fisher Scientific, Inc.), PicoGreen™ (Thermo Fisher Scientific, Inc.), SYBR™ Green (Thermo Fisher Scientific, Inc.), SYBR™ Green II (Thermo Fisher Scientific, Inc.), SYBR™ Gold (Thermo Fisher Scientific, Inc.), SYBR™ Safe DNA gel stain (Thermo Fisher Scientific, Inc.), CyQUANT™ GR dye (Thermo Fisher Scientific, Inc.), EvaGreen® (Biotium, Inc.), DAPI (4',6-diamidino-2-phenylindole), ethidium bromide, ethidium homodimer-1, ethidium homodimer-2, propidium iodide, dihydroethidium, hexidium iodide, DAPI, QuantiFluor® ssDNA dye (Promega Corp.), QuantiFluor® dsDNA dye (Promega Corp.), a benzothiazolium dye, acridine orange, proflavine HCl, thiazole orange, oxazole yellow, chromomycin A3, 7-aminoactinomycin D, hydroxystilbamidine, Hoechst 33258, Hoechst 33342, thiazole orange tetramethylpropane diamine, thiazole orange tetramethyl diamine, ethidium propane diamine, ethidium diethylene triamine, TOTO-1, TO-PRO-1, POPO-1, BOBO-1, YOYO-1, JOJO-1, POPO-3, LOLO-1, BOBO-3, YOYO-3, TOTO-3, PO-PRO-1, YO-PRO-1, JO-PRO-1, PO-PRO-3, YO-PRO-3, TO-PRO-3, TO-PRO-5, SYTOX™ Blue (Thermo Fisher Scientific, Inc.), SYTOX™ Green (Thermo Fisher Scientific, Inc.), SYTOX™ Orange (Thermo Fisher Scientific, Inc.), SYTOX™ Red (Thermo Fisher Scientific, Inc.), any of SYTO™ 40, 41, 42, or 45 (Thermo Fisher Scientific, Inc.), any of SYTO™ 9, 10, 11, 12, 13, 14, 16, 21, 24, or 25 (Thermo Fisher Scientific, Inc.), SYTO™ RNASelect (Thermo Fisher Scientific, Inc.), SYTO™ BC (Thermo Fisher Scientific, Inc.), any of SYTO™ 80, 81, 82, 83, 84, or 85 (Thermo Fisher Scientific, Inc.), any of SYTO™ 17, 59, 60, 61, 62, 63, or 64 (Thermo Fisher Scientific, Inc.), bis-(6-chloro-2-methoxy-9-acridinyl) spermine, quinacrine, 9-amino-6-chloro-2-methoxyacridine, LDS 751, daunomycin, mithramycin A, olivomycin, or chromomycin A3.

In some embodiments, the compound comprises at least one, two, or three water-solubilizing groups. These can be present in any of D, L, R, or a combination thereof. For example, negatively charged $SO_3$ groups are present in certain Alexa Fluor® moieties. Water-solubilizing groups can provide the benefits of allowing the compound to be used in aqueous solution and/or reducing or eliminating the degree to which the compound crosses intact cell membranes of live cells.

In some embodiments, the compound is a free acid or salt of any of the following:

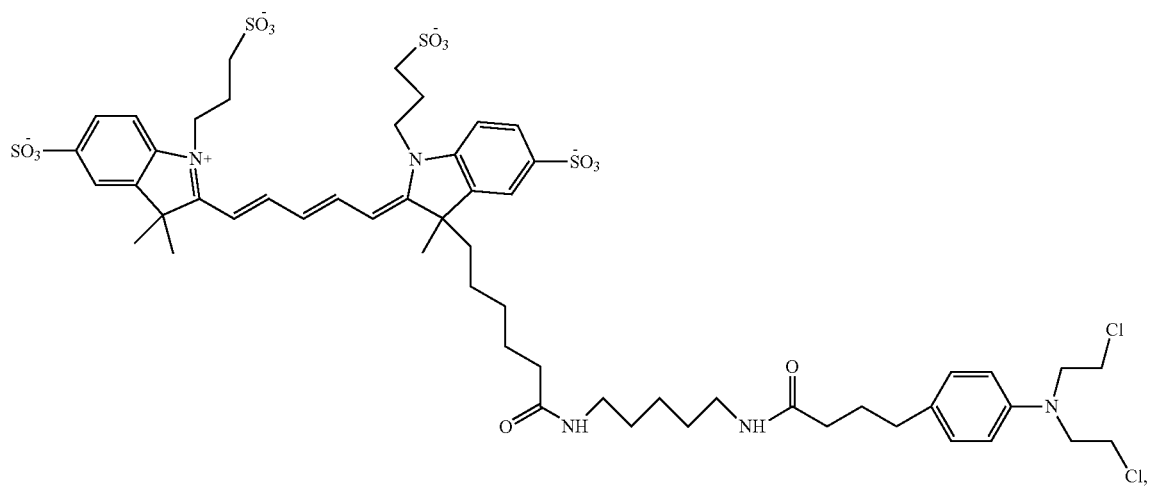

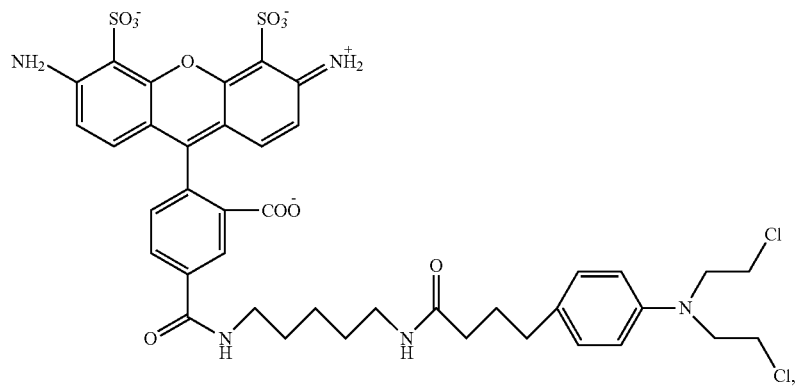
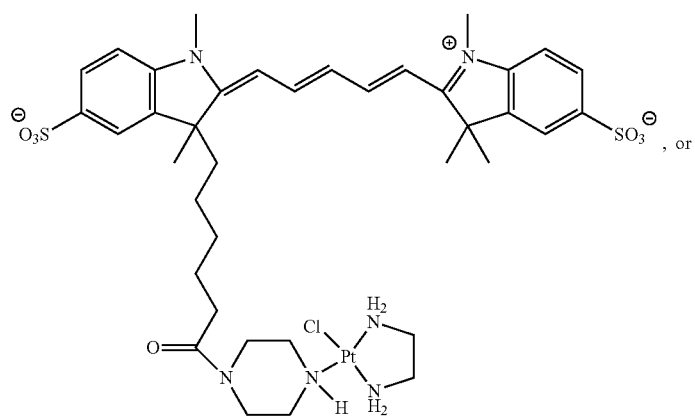
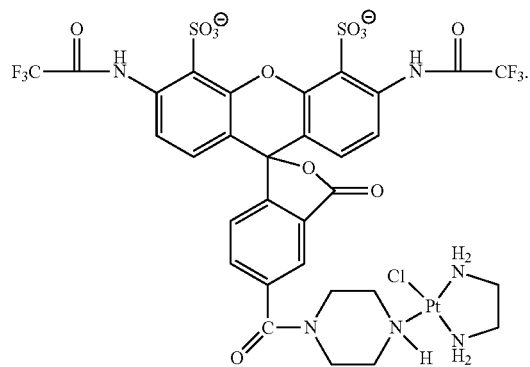

In some embodiments, the compound is a salt of any of the foregoing. In some embodiments, the compound is a biologically compatible salt of any of the foregoing.

In some embodiments, the compound is the following ("Compound 1"):

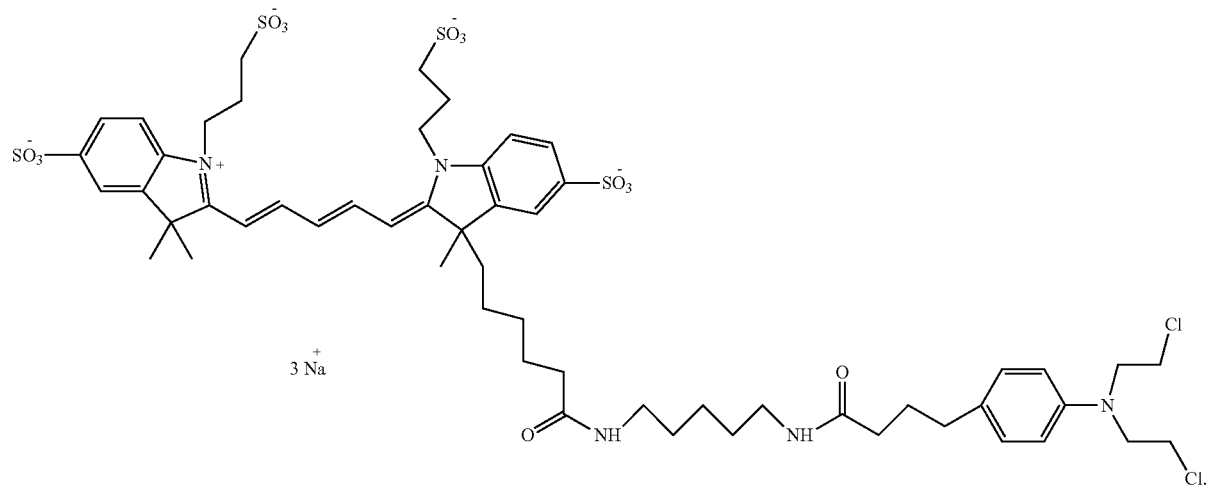

In some embodiments, the compound is the following ("Compound 2"):

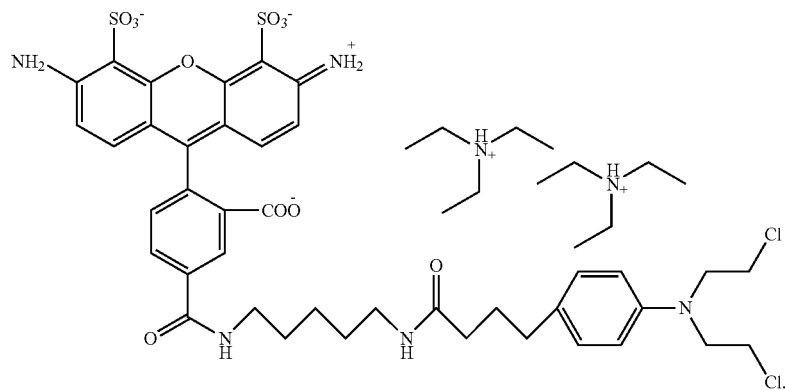

In some embodiments, the compound is the following ("Compound 3"):

In some embodiments, the compound is the following ("Compound 4"):

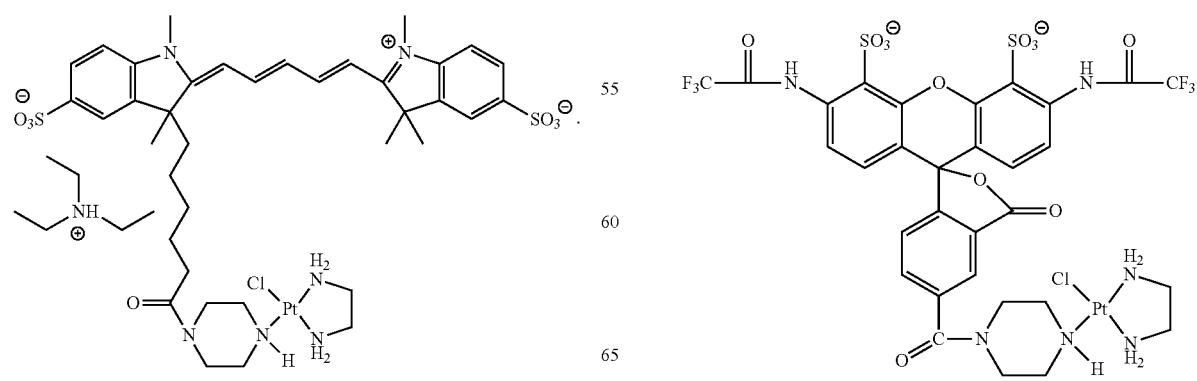

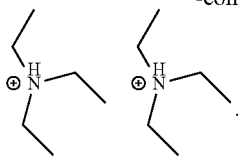

Those of skill in the art will appreciate that compounds may exhibit the phenomena of tautomerism, conformational isomerism, geometric isomerism and/or stereo isomerism. As the formulae drawings within this specification and claims cannot necessarily represent all of the possible tautomeric, conformational isomeric, enantiomeric or geometric isomeric forms, it should be understood that the disclosure encompasses any tautomeric, conformational isomeric, enantiomeric and/or geometric isomeric forms of the compounds having one or more of the utilities described herein.

In addition, it will also be apparent that the compounds may exist in many different protonation states, depending on, among other things, the pH of their environment. While the structural formulae provided herein depict the compounds in only one of several possible protonation states, it will be understood that these structures are illustrative only, and that the disclosure is not limited to any particular protonation state. Any and all protonated forms of the compounds are intended to fall within the scope of the disclosure.

Furthermore, the compounds of the disclosure may bear multiple positive or negative charges. The associated counter ions with the enzyme substrates are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the disclosure, and that the disclosure encompasses the compounds in association with any type of counter ion unless otherwise specified.

Certain embodiments provide a method, use, or composition for staining cells and/or assessing cell viability, being compatible for use with, for example, flow cytometry and fluorescence microscopy. Such methods and uses can comprise incubating a cell or mixture of cells with a compound disclosed herein; providing a stimulus to the cell or mixture of cells to elicit a fluorescent signal; and measuring the fluorescent signal. Methods and uses can further comprise quantifying the amount of live and/or dead cells, e.g., by determining whether the degree of fluorescence exceeds a predetermined threshold (indicating nonviability), or by grouping results into live and dead populations (where dead cell populations show a greater extent of staining given their compromised membrane integrity).

In some embodiments, cells are incubated with a compound disclosed herein in the presence of culture medium. In some embodiments, cells are incubated with a compound disclosed herein in the presence of extracellular protein, which can be present, for example, in a range of 1% to 20% protein in media. In some embodiments, a compound disclosed herein or a composition comprising such a compound is added to a culture medium comprising cells.

In some embodiments, the compound is delivered or passes into nonviable eukaryotic cells, e.g., mammalian cells, such as human cells. When the cells are illuminated with a light source, then fluorescence emissions can be collected, detected, analyzed, or measured. The cells in the assay may be treated with a substance or reagent that induces cell death, e.g., camptothecin or staurosporine. Data may be acquired using any appropriate fluorescence detection apparatus such as a plate reader, fluorescence microscope, or flow cytometer.

In some embodiments, the cell or mixture of cells is incubated with at least one, two, three, or four additional fluorescent molecules, wherein the at least one, two, three, or four additional fluorescent molecules are spectrally distinguishable from the compound of Formula I, and fluorescent signals are measured measuring from the at least one, two, three, or four additional fluorescent molecules. Fluorescence from two sources is considered spectrally distinguishable if the emission maxima are separated by at least 30 nm or if fluorescence from the sources can be distinguished through the use of optical filters, e.g., a pair of filters wherein fluorescence from at least one of the molecules is differentially reduced by at least one of the filters.

In another embodiment, the assay method may be conducted where cells are contained in a plurality of vessels. In any vessel, the cells may be of one type or different types of cells. The cells may be the same type grown under different conditions, e.g. in the presence of different media. Some of the cells may be treated with an apoptosis inducer or a caspase inhibitor. The plurality of vessels, an array, may be illuminated by a light source, e.g. a scanning light source. The cells may be of the same or different organisms.

In another aspect, kits are provided comprising a compound disclosed herein and one or more other reagents, such as a cytotoxic agent, apoptosis inducer, cells, a solvent, or a desiccant. Kits may include reagents useful to conduct the assay methods of the disclosure. In some embodiments, kits comprise at least one of an organic solvent and a desiccant. In some embodiments, the solvent is DMSO. The kit may also include eukaryotic cells. In some embodiments, the kit is compatible for use with flow cytometry. In some embodiments, the kit is compatible for use with fluorescence microscopy. In certain embodiments, the kits further comprise one or more of the following: a buffering agent, a purification medium, or a vial comprising a sample.

In certain embodiments, the kits disclosed herein comprise one or more of the compounds described herein and one or more containers in which to store the one or more compounds, and can further comprise at least one additional substance such as a solvent, buffer, stabilizer, pH adjusting agent, etc. The kit optionally contains instructions for how to prepare the one or more compounds or how to prepare a composition containing the one or more compounds, and how to administer the compound or composition containing the compound. In certain embodiments, the kit comprises instructions for performing a method disclosed herein. In some embodiments, the kit comprises instructions for performing a cell viability assay. In certain embodiments, the method is an in vitro method. The kit may further comprise one or more pieces of equipment to deliver the compound, or composition containing the compound including, but not limited to, syringes, pipettes, pipette bulbs, spatulas, vials, syringe needles, and various combinations thereof.

In certain embodiments, kits are provided, comprising:
(a) one or more of the compounds or compositions described herein;
(b) one or more containers; and optionally
(c) instructions for staining cells and/or assessing cell viability according to a method disclosed herein.

Compounds disclosed herein can be prepared using known chemistry. Exemplary methods in which a fluorescent moiety is linked to an R group of Formula IA or Formula IB are provided in certain Examples below. Those skilled in the art can adapt these methods for use with various fluorescent moieties and R groups.

A general protocol for conjugating a fluorescent moiety in the form of an N-hydroxy succinimide (NHS) ester to a linker or R group with a nucleophilic group (e.g., amino group or sulfhydryl) entails dissolving the NHS esters in aqueous acetonitrile or DMSO (the percentage of acetonitrile or DMSO is determined by the hydrophobicity of the dye to attain solubility) with linker in water (or aqueous acetonitrile or DMSO solution if the linker is hydrophobic). Aqueous sodium bicarbonate buffer (1M) is added to the solution to achieve 0.1M buffer concentration while vortexing or shaking. The mixture is shaken at room temperature for 10 minutes to 30 minutes. The crude conjugate in the reaction mixture can be purified by reverse-phase HPLC.

The general protocol described in the above paragraph can also be used for conjugating an R group of Formula IA to a linker or fluorescent moiety.

A general protocol for conjugating an R group of Formula IB to a linker or fluorescent moiety entails nucleophilic addition of the R group to an electrophile and is described, for example, in the ULYSIS® Nucleic Acid Labeling Kit User Guide (Thermo Fisher Scientific, MAN0002212, MP21650, Revision A.0, 2015, herein incorporated by reference in its entirety). Briefly, ULSYS® Nucleic Acid Labeling kits provide a non-enzymatic method for chemically labeling purine bases in nucleic acids with fluorescent dyes. The method, the Universal Linkage System (ULS®), is based on the use of a platinum dye complex that forms a stable adduct with the N7 position of guanine and, to a lesser extent, adenine bases in DNA, RNA, PNA and oligonucleotides.

Alternative approaches are possible as well. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |

TABLE 1-continued

Examples of some routes to useful covalent linkages

| Electrophilic Group | Nucleophilic Group | Resulting Covalent Linkage |
|---|---|---|
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a suitable leaving group (e.g., succinimidyloxy (—OC$_4$H$_4$O$_2$), sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^x$ or —OCNR$^x$NHR$^y$, where R$^x$ and R$^y$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).

**Acyl azides can also rearrange to isocyanates.

The choice of the reactive group used to form a covalent linkage typically depends on the reactive or functional group on the substance to be conjugated and the type or length of covalent linkage desired. The types of functional groups typically present include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. In certain embodiments, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. As used herein, "reactive platinum complex" refers to chemically reactive platinum complexes such as described in U.S. Pat. No. 5,714,327, herein incorporated by reference in its entirety.

VI. EXAMPLES

The following are examples of methods, uses, and compositions disclosed herein. It is understood that various other embodiments may be practiced, given the general and detailed descriptions provided above. The following examples are given for the purpose of illustrating the present teachings and shall not be construed as being a limitation on the scope of the disclosure or claims.

All staining procedures described below were performed at room temperature unless otherwise indicated. Flow cytometric analysis of stained cells was performed according to standard techniques.

A. Synthesis of Compounds

Compound 1, shown below, was synthesized as follows.

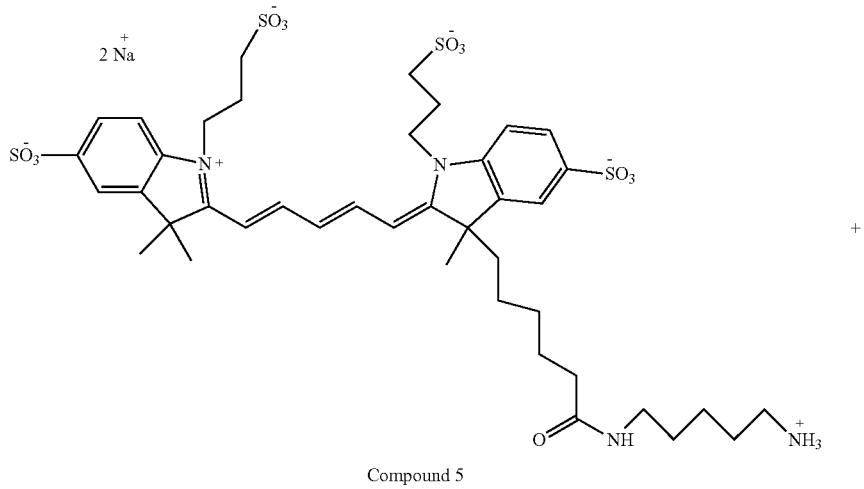

Compound 5

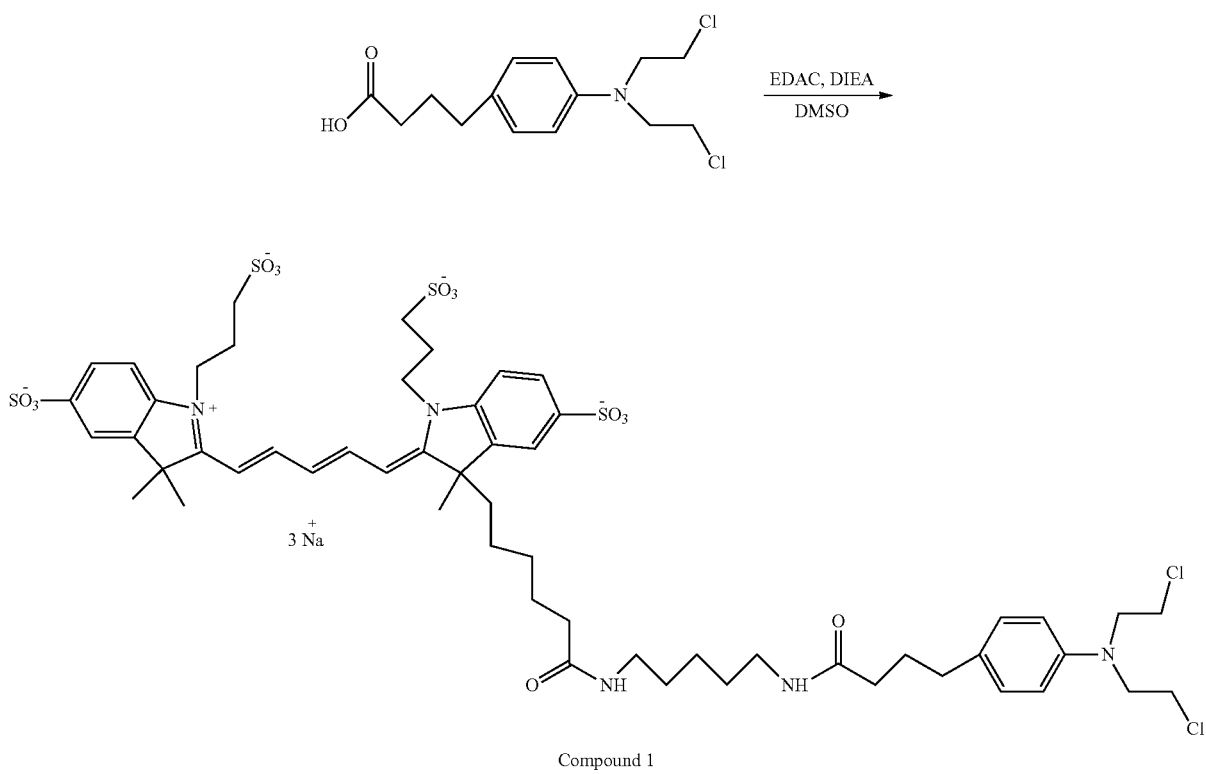

Compound 1

Compound 5 cadaverine disodium salt (10 mg, 0.01 mmole), Chloroambucil (5 mg, 0.015 mmole), EDAC (3 mg, 0.015 mmole) and DIEA (5 µL, 0.029 mmole) were placed in a round bottom flask. To the flask was added 1 mL DMSO, and the mixture was stirred for 24 hours. TLC (chloroform/methanol/water, 65:30:5) showed that the reaction completed. A mixed solvent of ether-hexane (1:1, 15 mL) was added to the reaction mixture and stirred for 10 min. The stirring was stopped and the two phase mixture was allowed to settle down. Then solvent was removed with a pipette. The wash process was repeated one more time. The residue was then stirred with ether (15 mL) for 10 minutes and the solvent was removed with a pipette after the two phase mixture was allowed to settle down. The ether wash process was repeated twice. The residue was finally washed with chloroform 5 times. Each time the residue was stirred with chloroform (15 mL) for 10 minutes, then the mixture was allowed to settle down and the solvent was removed with a pipette. The blue solid was dried under high vacuum for two hours to give 12 mg of the desired product, Compound 1 (Yield: 92%).

Compound 2, shown below, was synthesized in three steps using the following scheme.

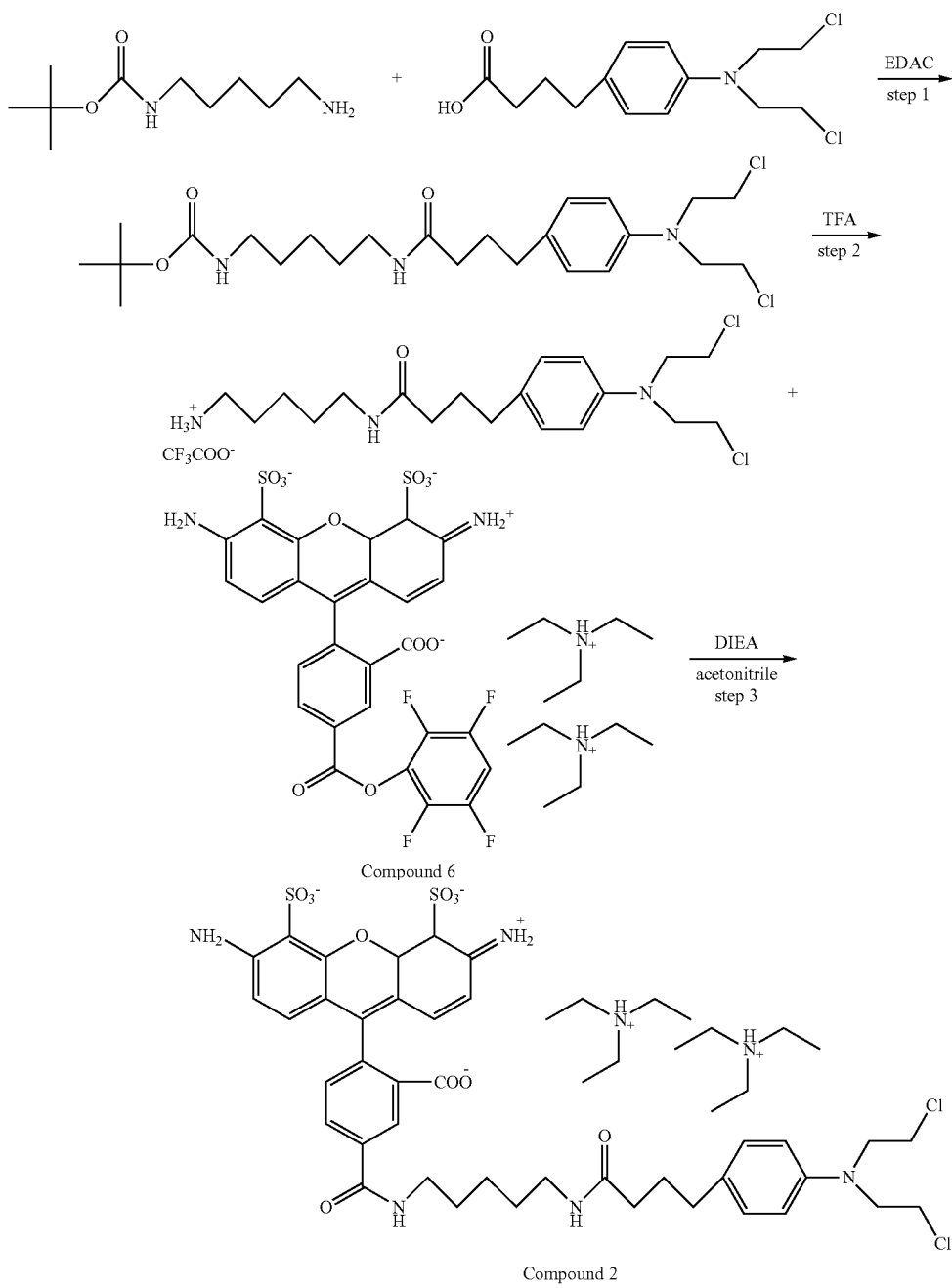

Compound 6

Compound 2

Step 1: N-Boc-cadaverine (67 mg, 0.329 mmole), 4-(4-(bis(2-chloroethyl)amino)phenyl)butanoic acid (Chloroambucil) (100 mg, 0.329 mmole) and EDAC (76 mg, 0.395 mmole) were placed in a one-neck 100 ml round bottom reaction flask. Dichloromethane (15 mL) was added to the reaction flask. The mixture was stirred at room temperature for 18 hours. TLC (20% ethyl acetate in hexane) showed the completion of the reaction. The solvent was evaporated and the product was purified by column chromatography on Biotage (SNAP 50 g silica gel column) eluted with 0-5% methanol in chloroform. The desired fractions were collected and evaporated to give 120 mg product (t-butyl (5-(4-(4-(bis(2-chloroethyl)amino)phenyl)butanamido) pentyl)carbamate) in 63% yield.

Step 2: t-Butyl (5-(4-(4-(bis(2-chloroethyl)amino)phenyl) butanamido)pentyl) carbamate (50 mg, 0.102 mmole) was mixed with 150 µL TFA in 10 mL dichloromethane in a 50 mL one-neck round bottom flask. The reaction mixture was stirred for three hours. TLC (50% ethyl acetate in hexane) showed the completion of the reaction. The solvent was evaporated on rotary evaporator. The product was further dried under high vacuum for 3 hours. About 50 mg of the product was obtained (Yield: 98%). The product was used for next step without further purification.

Step 3: Compound 6 (10 mg, 0.0113 mmole) and N-(5-aminopentyl)-4-(4-(bis(2-chloroethyl)amino)phenyl)butanamide trifluoroacetate (5.6 mg, 0.0113 mmole) were added into a 50 mL round bottom reaction flask. Dry acetonitrile (1 mL) was added followed by the addition of DIEA (2 µL, 0.0135 mmole). The reaction mixture is stirred for 5 hours. TLC (10% MoOD in chloroform and 5% water in acetonitrile) showed the completion of the reaction. The product was purified by reverse phase column chromatography (SNAP C18 12 g column on Biotage). After collecting the desired fractions and evaporation of the solvent. 6 mg of the product (Compound 2) was obtained (58% yield).

Compound 3 and Compound 4, both shown below, were synthesized according to manufacturer instructions in the ULYSIS® Nucleic Acid Labeling Kit User Guide (Thermo Fisher Scientific, MAN0002212, MP21650, Revision A.0, 2015, herein incorporated by reference in its entirety).

by flow cytometry with or without a washing step. Results are shown as median fluorescence (arbitrary units) of live and dead cell populations in Table 2. Signal-to-noise ratio (S:N) indicates the fold increase in signal for median fluorescence of dead cells versus live cells.

TABLE 2

Live and Dead Cell Median Fluorescence with Compound 1

| | No Wash | | | Wash | | |
|---|---|---|---|---|---|---|
| | Dead Cells | Live Cells | S:N | Dead Cells | Live Cells | S:N |
| Control (Sytox ™ Red) | 23977 | 711 | 34 | 5052 | 105 | 48 |
| PBS 1 drop | 21785 | 578 | 38 | 4077 | 85 | 48 |
| PBS 2 drops | 25839 | 876 | 29 | 6804 | 140 | 49 |
| Water 1 drop | 21560 | 608 | 35 | 4078 | 93 | 44 |
| Water 2 drops | 25190 | 869 | 29 | 6738 | 135 | 50 |

C. Flow Cytometric Analysis of Live and Heat-Treated Jurkat Cells Labeled with Compound 4 and Compound 2

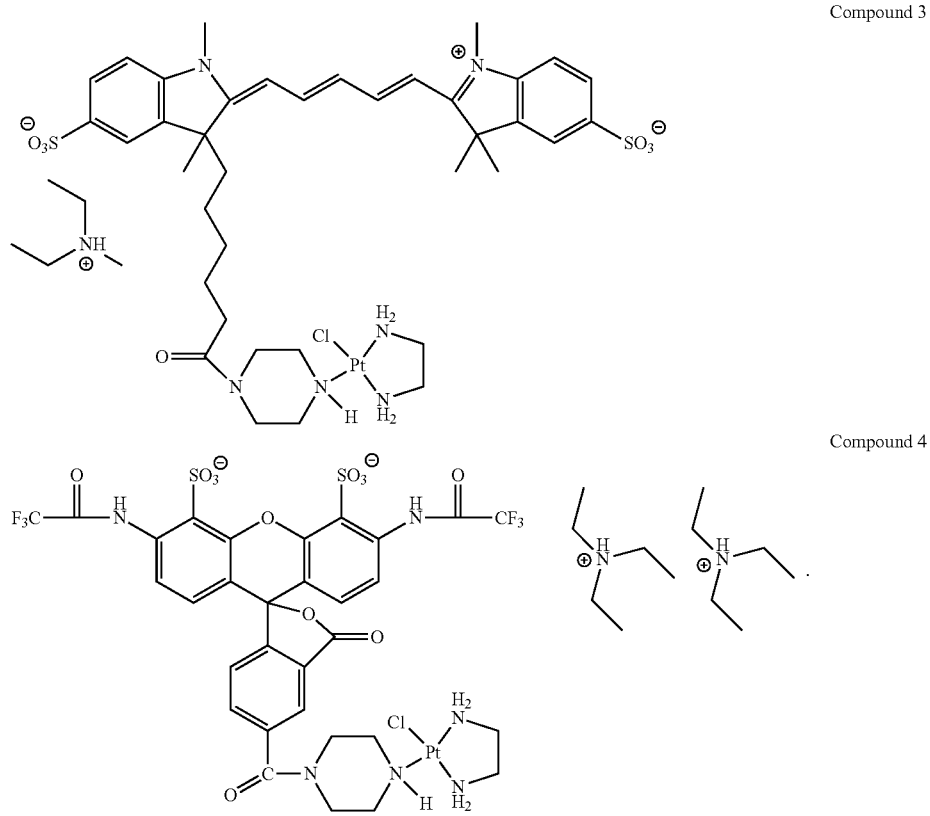

B. Flow Cytometric Analysis of Live and Dead Cells Labeled with Compound 1

A mixture of live and dead Jurkat cells were suspended in phosphate-buffered saline ("PBS") or water, with 1 or 2 drops of DMSO from a dropper bottle added (approx. 41-42 µl per drop), and stained for 10 minutes with 25 µM Compound 1. A control staining was performed according to manufacturer instructions (staining period is typically 5-20 minutes, in this particular experiment the staining period was 5 minutes) with Sytox™ Red Dead Cell Stain (Thermo Fisher Scientific Cat. No. S34859). Samples were analyzed Jurkat cells were heat treated at 60° C. or left untreated, mixed together in equal proportions, and stained with Compound 4 or Compound 2. Staining with Compound 4 was at 25 µM concentration of dye for 1-5 minutes. Staining with Compound 2 was at 25 µM concentration of dye for 5 minutes. Comparative samples were stained with the LIVE/DEAD® Fixable Green Dead Cell Stain Kit (Thermo Fisher Scientific Cat. No. L23101). Each staining was performed in PBS and in complete media (Roswell Park Memorial Institute medium supplemented with 10% fetal bovine serum; "RPMI+10FBS").

Figure 1A:
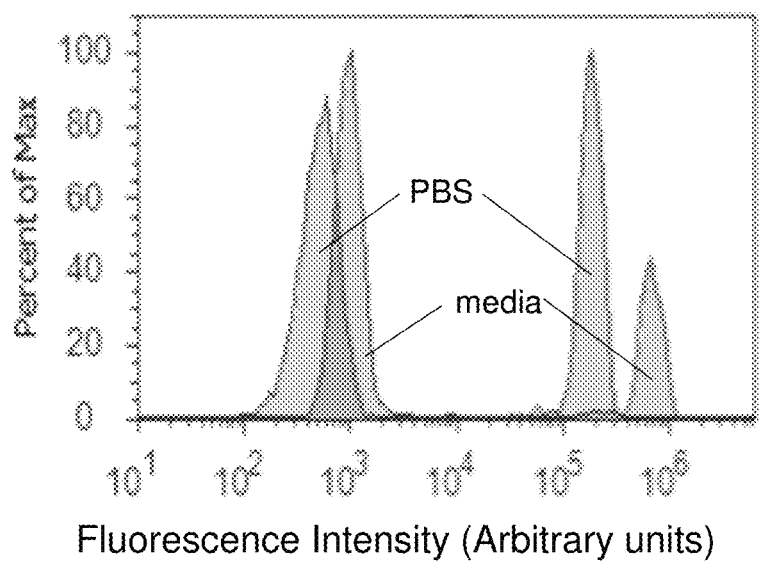
FIG. 1A shows results of staining with the LIVE/DEAD® Fixable Green Dead Cell Stain Kit in phosphate buffered saline (PBS) (first and third peaks from left) and in media (second and fourth peaks from left). The first and second peaks from left represent live cells and the third and fourth peaks from left represent dead cells.
Figure 1B:
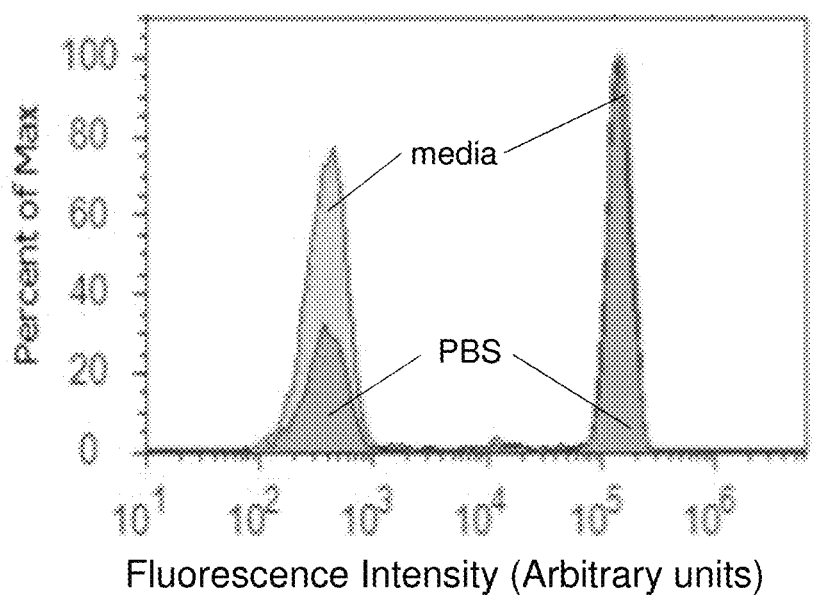
FIG. 1B shows results of staining with Compound 4 in media and in PBS. The peaks for the two conditions overlap, with the left peaks representing live cells and the right peaks representing dead cells.
Figure 1C:
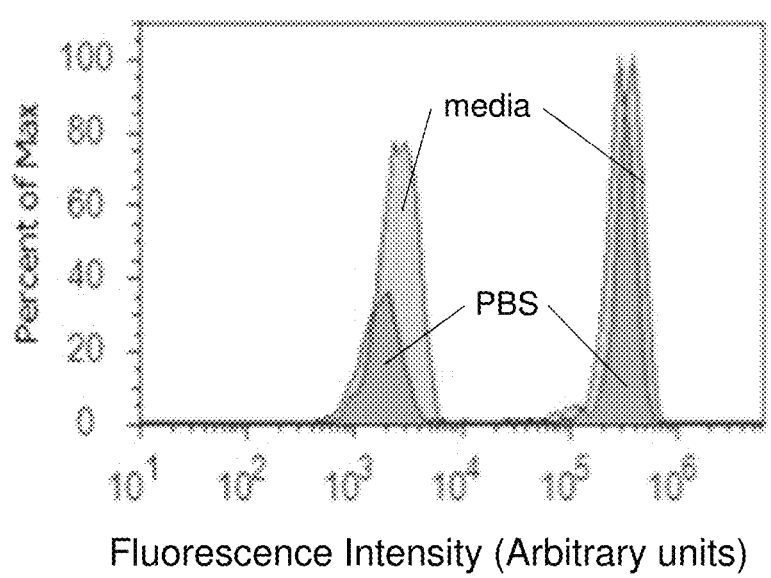
FIG. 1C shows results of staining with Compound 2 in media and in PBS. The peaks for the two conditions overlap, with the left peaks representing live cells and the right peaks representing dead cells.

Cells were analyzed by flow cytometry using 488 nm excitation with 530/30 nm emission filter. Histograms (FIGS. 1A-1C) showed separation of live cells (left peaks in FIGS. 1A-1C) and dead cells (right peaks in FIGS. 1A-1C). Compounds 2 and 4 (FIGS. 1B-1C; Compound 4 and Compound 2, respectively) showed clear separation of live and dead cells when stained in PBS and when stained in complete media, with little to no variation in intensity of staining due to the presence of complete media.

D. Flow Cytometric Analysis of Live and Heat-Treated Jurkat Cells after Fixation and/or Permeabilization Labeled with Compound 4 and Compound 2

Fixation with reagents such as formaldehyde and ethanol and/or permeabilization with detergents, used, e.g., in intracellular phosphorylation studies, can cause loss of sensitivity with some dead cell discriminator stains. Compounds disclosed herein were tested in protocols including fixation and/or permeabilization as follows.

50% live/50% dead Jurkat cell mixtures in either PBS or complete media were fixed with 4% formaldehyde and stained with Compound 4 or Compound 2, and analyzed by flow cytometry. Staining with Compound 4 was at 25 µM concentration of dye for 1-5 minutes. Staining with Compound 2 was at 25 µM concentration of dye for 5-10 minutes.

Figure 2A:
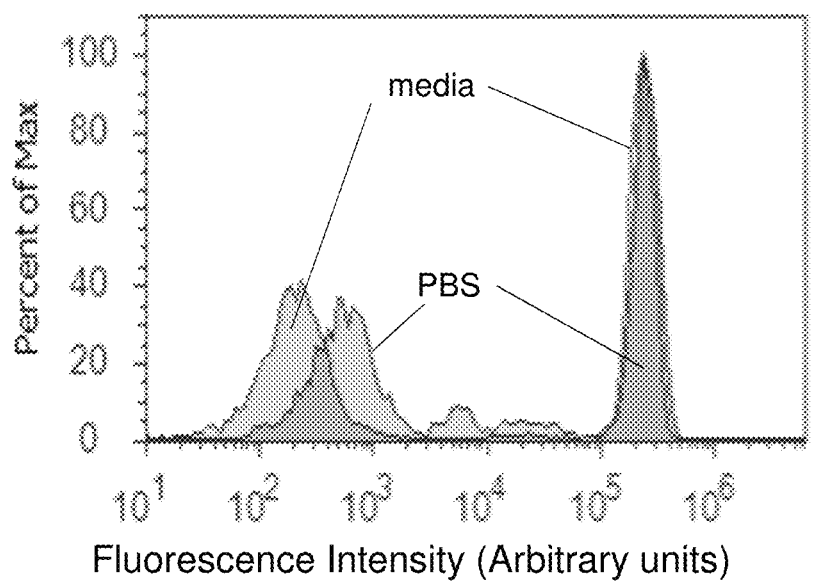
FIG. 2A shows results of staining fixed cells with Compound 4 in media and in PBS. The peaks for dead cells at right overlap, with the first and second peaks representing live cells in media and PBS, respectively.
Figure 2B:
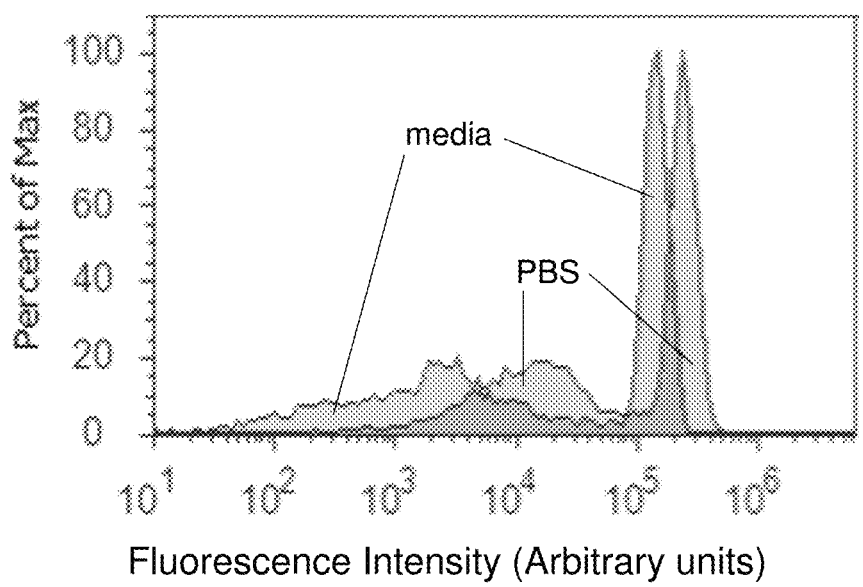
FIG. 2B shows results of staining fixed cells with Compound 2 in media (first and third peaks from left) and in PBS (second and fourth peaks from left). The first and second peaks represent live cells and the third and fourth peaks from left represent dead cells.

Results are shown in FIGS. 2A-2B (Compound 4 and Compound 2, respectively). Clear, sharp peaks in these plots corresponded to dead cells. Live cells were distributed somewhat more broadly with a substantial majority of live cells showing two logs of separation from the dead cells.

50% live/50% dead Jurkat cell mixtures in either PBS or complete media were fixed with 4% formaldehyde, permeabilized with 1 mL of 1% BSA in PBS per sample ($1 \times 10^6$ cells/mL), and stained with Compound 4 or Compound 2, and analyzed by flow cytometry. Staining with Compound 4 was at Staining with Compound 4 was at 25 µM concentration of dye for 1-5 minutes. Staining with Compound 2 was at 25 µM concentration of dye for 5-10 minutes.

Results are shown in FIGS. 3A-3B (Compound 4 and Compound 2, respectively). Clear, sharp peaks in these plots corresponded to dead cells and live cells were distributed somewhat more broadly with a substantial majority of live cells showing two logs of separation from the dead cells.

E. Flow Cytometric Analysis of Live and Heat-Treated Jurkat Cells Labeled with Compound 2

Populations of untreated Jurkat cells in either PBS or complete media were incubated with 25 µM Compound 2 for five minutes and analyzed by flow cytometry. Results are shown in FIGS. 4A-4B (PBS and complete media, respectively). Small strongly labeled peaks (7-14% of total cells) corresponding to dead cells were observed and showed separation from the major live cell peaks in both conditions.

Mixed populations of untreated and heat-killed Jurkat cells in equal proportions, in either PBS or complete media, were treated with 25 µM Compound 1 for five minutes and analyzed by flow cytometry. Results are shown in FIGS. 5A-5B (PBS and complete media, respectively). Strongly labeled peaks (34-36% of total cells) corresponding to dead cells were observed and showed separation from the live cell peaks in both conditions.

Comparative experiments were performed with mixed populations of untreated and heat-killed Jurkat cells in equal proportions in either PBS or complete media, using the LIVE/DEAD® Fixable Green Dead Cell Stain Kit (Thermo Fisher Scientific Cat. No. L23101) including a 30 minute staining time per manufacturer's instructions, gave good agreement with the results discussed above; 32-34% of cells were strongly labeled, indicative of dead cells (not shown).

These data indicate that Compound 1 can rapidly and reliably stain dead cells differentially from live cells with similar performance in PBS and in complete media.

F. Flow Cytometric Analysis of Live and Heat-Treated Jurkat Cells Fixed, Permeabilized, and Labeled with Compound 1

Populations of untreated Jurkat cells in either PBS or complete media were fixed and permeabilized as described above and treated with 25 µM Compound 1 for five minutes, then analyzed by flow cytometry. Results are shown in FIGS. 6A-6B. Small strongly labeled peaks (7-9% of total cells) corresponding to dead cells were observed and showed separation from the major live cell peaks in both conditions.

Mixed populations of untreated and heat-killed Jurkat cells in equal proportions, in either PBS or complete media, were fixed and permeabilized as described above and treated with 25 µM Compound 1 for five minutes, then analyzed by flow cytometry. Results are shown in FIGS. 7A-7B. Strongly labeled peaks (35-39% of total cells) corresponding to dead cells were observed and showed separation from the live cell peaks in both conditions.

These data indicate that Compound 1 can rapidly stain dead, fixed, permeabilized cells differentially from live cells with similar performance in PBS and in complete media.

G. Rapid Staining of dead cells at various concentrations of Compound 4 and Compound 2

Mixed populations of untreated and heat-killed Jurkat cells in equal proportions in complete media were treated with Compound 4 at 6.25 µM, 12.5 µM, or 25 µM for five minutes, and then analyzed by flow cytometry. Staining was performed either before or after fixation and permeabilization as described above. An untreated control was also analyzed (after fixation and permeabilization only). Results are shown in FIG. 8A (before fixation and permeabilization) and FIG. 8B (after fixation and permeabilization). Strongly labeled peaks corresponding to dead cells were observed and showed good separation from the live cell peaks in all stained conditions. The fluorescence intensity of the unstained control sample was similar to the live cell peaks for all stained conditions, indicating that staining of live cells was negligible. The experiment was repeated, except with a 10 minute staining time, and results were similar (data not shown).

Mixed populations of untreated and heat-killed Jurkat cells in equal proportions in complete media were treated with Compound 2 at 25 µM, 12.5 µM, or 6.25 µM for five minutes, and then analyzed by flow cytometry. Staining was performed either before or after fixation and permeabilization as described above. An untreated control was also analyzed (live cells for before fixation and permeabilization; mixed live and heat-killed cells after fixation and permeabilization). Results are shown in FIG. 9A (before fixation and permeabilization) and FIG. 9B (after fixation and permeabilization). Strongly labeled peaks corresponding to dead cells were observed and showed good separation from the live cell peaks in all stained conditions. The fluorescence intensity of the unstained control sample was similar to the live cell peaks for the after fixation and permeabilization conditions, indicating that staining of live cells was negligible. The fluorescence intensity of the unstained control sample was modestly lower than the live cell peaks for the before fixation and permeabilization conditions (about 1-1.5 logs difference from peak to peak in a concentration-correlated manner), indicating that low-level staining of live cells occurred which did not interfere with distinguishing them from dead cells, which were nonetheless separated by over 2 logs from peak to peak. The experiment was repeated, except with a 10 minute staining time, and results were similar (data not shown).

These data indicate that Compound 4 and Compound 2 can rapidly stain dead cells before or after fixation and permeabilization differentially from live cells over a range of concentrations.

H. Detection of Dead Cells Following Camptothecin and Staurosporine Treatment

Ramos cells were treated overnight with 10 μM camptothecin or 1 μM staurosporine. Staining used 25 μM Compound 4 for 30 minutes in complete media. Aliquots were fixed, or fixed and permeabilized. Results are shown as follows: untreated controls in FIGS. 10A-10B; camptothecin-treated cells in FIGS. 10C-10D; and staurosporine-treated cells in FIGS. 10E-10F. Cells in FIGS. 10A, 10C, and 10E were fixed, and cells in FIGS. 10B, 10D, and 10F were fixed and permeabilized. The number of dead cells detected is shown in the figures and indicates that cell killing by camptothecin and staurosporine could be detected by using Compound 4 staining in complete media. Permeabilization had only a marginal effect on the results, indicating that cell viability can be assessed regardless of whether cells are permeabilized after treatment with Compound 4.

Although the foregoing disclosure has been described in some detail by way of illustration and example for purposes of clarity of understanding, the descriptions and examples should not be construed as limiting the scope of the invention.

What is claimed is:

1. A compound of Formula I:

D-L-R (I)

wherein:
D is a fluorescent moiety;
L is a linker; and
R is Formula IA:

—B—N($R^1$)($R^2$) (Formula IA), wherein B is a bond, an aliphatic group or an aromatic group; and
$R^1$ and $R^2$ are each independently ethyl substituted with a Z at the 2 position or substituted ethyl further substituted with a Z at the 2 position, and each Z is independently OH, Cl, Br, I or

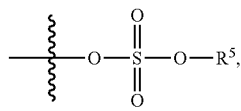

where $R^5$ is alkyl, substituted alkyl, aryl or substituted aryl.

2. The compound of claim 1, wherein R is Formula IA.
3. The compound of claim 1, wherein B is aryl, substituted aryl, heteroaryl, or substituted heteroaryl.
4. The compound of claim 1, wherein R is

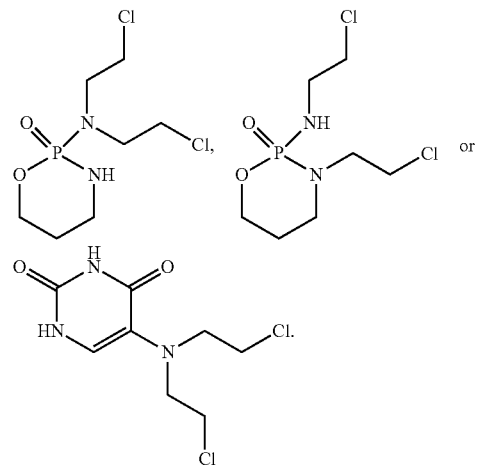

5. The compound of claim 1, wherein B is a six-membered aryl, substituted aryl, heteroaryl, or substituted heteroaryl.
6. The compound of claim 1, wherein B is phenyl, substituted phenyl, pyridinyl, or substituted pyridinyl.
7. The compound of claim 1, wherein D is a xanthene dye, a cyanine dye, a phenanthridinium dye, a bisbenzimide dye, a bisbenzimidazole dye, an acridine dye, a chromomycinone dye or a benzothiazolium dye.
8. The compound of claim 1, which comprises at least one, two, or three water-solubilizing groups.
9. The compound of claim 1, which is a free acid or salt of any one of:

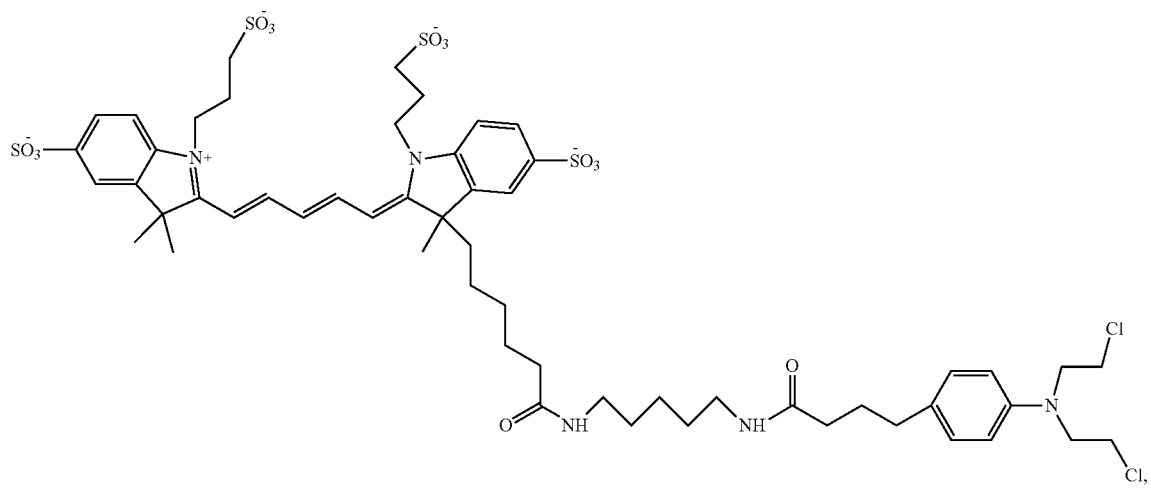

or

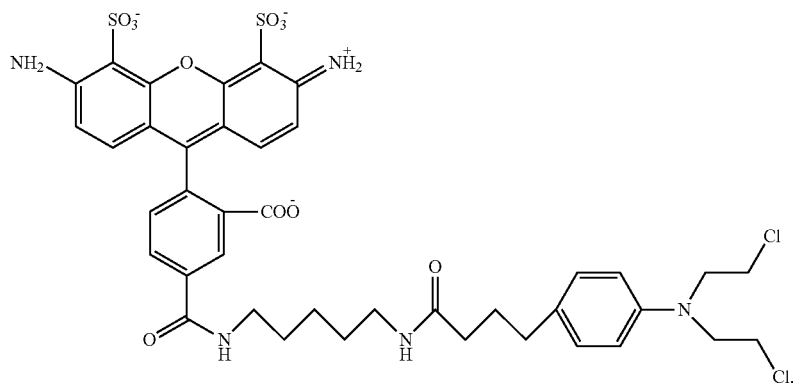

10. A composition comprising the compound of claim 1 and at least one solvent.

11. A kit comprising the compound of claim 1.

12. A method for staining cells or assessing cell viability, comprising the steps of:
   a) incubating a cell or mixture of cells with the compound of claim 1;
   b) providing a stimulus to the cell or mixture of cells to elicit a fluorescent signal; and
   c) measuring the fluorescent signal.

13. The method of claim 12, wherein a mixture of live and dead cells are incubated with the compound.

14. The method of claim 13, further comprising determining the number or proportion of live and/or dead cells in the mixture.

15. The method of claim 12, wherein the incubating step is performed in cell culture media.

16. A method of assessing cell viability, comprising:
   a) providing a stimulus to the composition of claim 1 to elicit a fluorescent signal; and
   b) measuring the fluorescent signal.

17. The method of claim 12, wherein the measuring step is performed in cell culture media.

* * * * *

UNITED STATES PATENT AND TRADEMARK OFFICE
CERTIFICATE OF CORRECTION

PATENT NO. : 11,493,446 B2  
APPLICATION NO. : 16/205702  
DATED : November 8, 2022  
INVENTOR(S) : Kyle Gee Page 1 of 1

It is certified that error appears in the above-identified patent and that said Letters Patent is hereby corrected as shown below:

In the Claims

In Column 46, Claim 16, Line 26, delete "composition of claim 1" and insert -- compound of claim 1 --, therefor.

Signed and Sealed this  
Twenty-fourth Day of January, 2023

Katherine Kelly Vidal  
*Director of the United States Patent and Trademark Office*